US010793601B2

(12) United States Patent
Liu et al.

(10) Patent No.: US 10,793,601 B2
(45) Date of Patent: Oct. 6, 2020

(54) THERAPEUTIC SPALT-LIKE TRANSCRIPTION FACTOR 4 (SALL4) PEPTIDE

(71) Applicants: National University of Singapore, Singapore (SG); The Brigham and Women's Hospital, Inc., Boston, MA (US); Agency for Science, Technology and Research, Singapore (SG)

(72) Inventors: Bee Hui Liu, Singapore (SG); Daniel Geoffrey Tenen, Singapore (SG); Li Chai, Boston, MA (US); Cheng San Brian Chia, Singapore (SG); Anders Poulsen, Singapore (SG)

(73) Assignees: National University of Singapore, Singapore (SG); The Brigham and Women's Hospital, Inc., Boston, MA (US); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/095,603

(22) PCT Filed: Apr. 28, 2017

(86) PCT No.: PCT/US2017/030164
§ 371 (c)(1),
(2) Date: Oct. 22, 2018

(87) PCT Pub. No.: WO2017/190032
PCT Pub. Date: Nov. 2, 2017

(65) Prior Publication Data
US 2019/0218253 A1 Jul. 18, 2019

Related U.S. Application Data

(60) Provisional application No. 62/329,010, filed on Apr. 28, 2016.

(51) Int. Cl.
*A61K 38/00* (2006.01)
*A61K 38/08* (2019.01)
*C07K 7/06* (2006.01)
*C07K 7/08* (2006.01)

(52) U.S. Cl.
CPC .................. *C07K 7/06* (2013.01); *C07K 7/08* (2013.01); *A61K 38/00* (2013.01); *C07K 2319/033* (2013.01)

(58) Field of Classification Search
CPC .......... A61K 38/00; A61K 38/08; C07K 7/06; C07K 7/08; C07K 2319/033
USPC ........... 514/1.1, 19.3, 21.6, 21.7, 21.8, 21.9, 514/21.91; 530/300, 327, 328, 329, 330, 530/331
See application file for complete search history.

(56) References Cited

U.S. PATENT DOCUMENTS

| | | | |
|---|---|---|---|
| 3,719,667 A | 3/1973 | Gutowski | |
| 3,840,556 A | 10/1974 | Kukolja | |
| 6,686,333 B1* | 2/2004 | Kashanchi | C07K 14/005 424/93.6 |
| 7,790,407 B2 | 9/2010 | Ma | |
| 9,309,496 B2 | 4/2016 | Ma | |
| 2003/0153504 A1* | 8/2003 | Center | A61K 38/13 514/21.7 |
| 2005/0136040 A1* | 6/2005 | Hart | C12N 15/113 424/93.21 |
| 2015/0080315 A1 | 3/2015 | Chai et al. | |
| 2015/0211004 A1 | 7/2015 | Stewart | |

FOREIGN PATENT DOCUMENTS

WO 2015102536 A1 7/2015

OTHER PUBLICATIONS

Yampolsky et al., "THe Exchageability of Amino Acids in Proteins," Genetics, 170: 1459-1472. (Year: 2005).*
Yong et al., "Oncofetal Gene SALL4 in Aggressive Hepatocellular Carcinoma", The New England Journal of Medicine, Jun. 13, 2013, pp. 2266-2276, 368;24, DOI: 10.1056/NEJMoa1300297.
Ma et al., "CD133+ HCC cancer stem cells confer chemoresistance by preferential expression of the Akt/PKB survival pathway", Oncogene (2008) 27, 1749-1758; doi:10.1038/sj.onc.1210811; published online Sep. 24, 2007.
Liu et al., "Structure guided design of a therapeutic inhibitor of SALL4-NuRD in liver cancer", J Cancer Sci Ther 2017, 9:4 (Suppl); http://dx.doi.org/10.4172/1948-5956-C1-100.
Li et al., "CD133+ liver cancer stem cells resist interferon-gamma-induced autophagy", BMC Cancer (2016) 16:15; DOI 10.1186/s12885-016-2050-6.
Gao et al., "Targeting transcription factor SALL4 in acute myeloid leukemia by interrupting its interaction with an epigenetic complex", Blood, Feb. 21, 2013 vol. 121, No. 8; DOI 10.1182/blood-2012-04-424275.

(Continued)

*Primary Examiner* — Julie Ha
(74) *Attorney, Agent, or Firm* — Fish & Richardson P.C.

(57) ABSTRACT

Isolated peptides and pharmaceutical compositions comprising isolated peptides that bind to retinoblastoma binding protein 4 (RBBp4) and block the Spalt-Like Transcription Factor 4 (SALL4)-RBBp4 interaction are described. Methods of inhibiting binding of SALL4 to RBBp4 and methods of treating a subject having a disorder mediated by a dysregulation of SALL4 are also described.

31 Claims, 19 Drawing Sheets
Specification includes a Sequence Listing.

(56) References Cited

OTHER PUBLICATIONS

Notification Concerning Transmittal of International Preliminary Report on Patentability for International Application No. PCT/US2017/030164, "Therapeutic SALL4 Peptide", date of Issuance: Oct. 30, 2018.
Notification of Transmittal of the International Search Report and the Written Opinion of International Preliminary Report on Patentability for International Application No. PCT/US2017/030164, "Therapeutic SALL4 Peptide", dated Oct. 19, 2017.

\* cited by examiner i) PEN     : RQIKIWFQNRRMKWKK
ii) PEN-WT  : RQIKIWFQNRRMKWKK-MSRRKQAKPQHI
iii) PEN-MUT : RQIKIWFQNRRMKWKK-MSARAQAKPQHI
iv) PEN-FFW : RQIKIWFQNRRMKWKK-RRKFAKFQWI

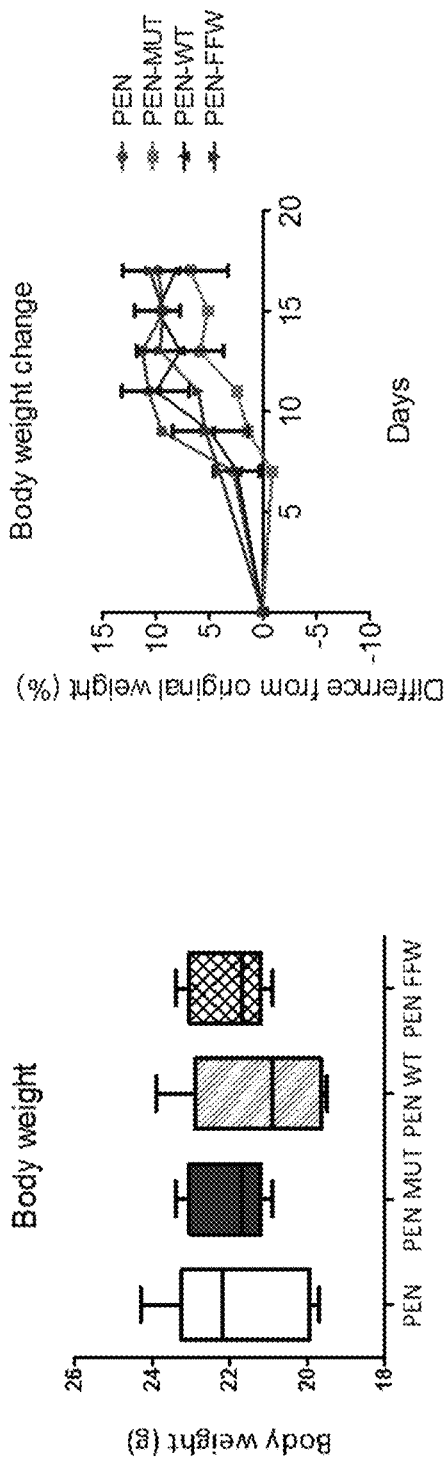
FIG. 9C
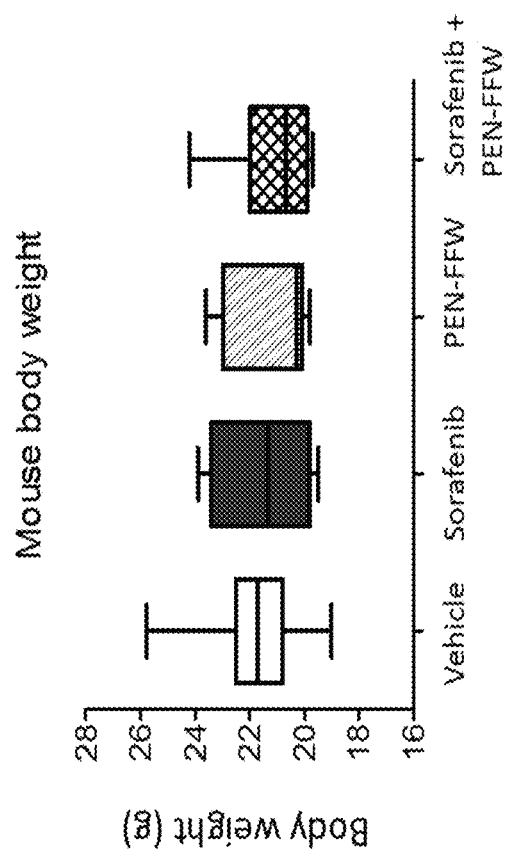
FIG. 9D
FIG. 9E

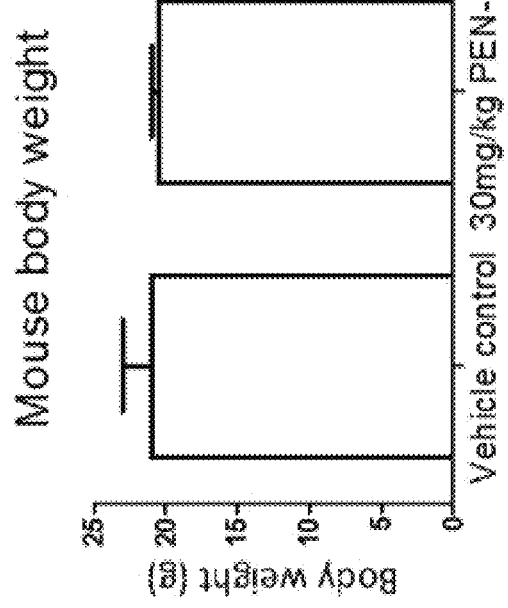
FIG. 11A
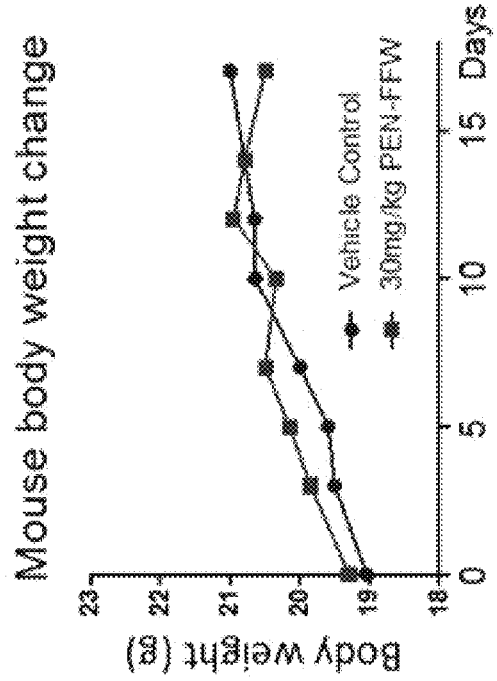
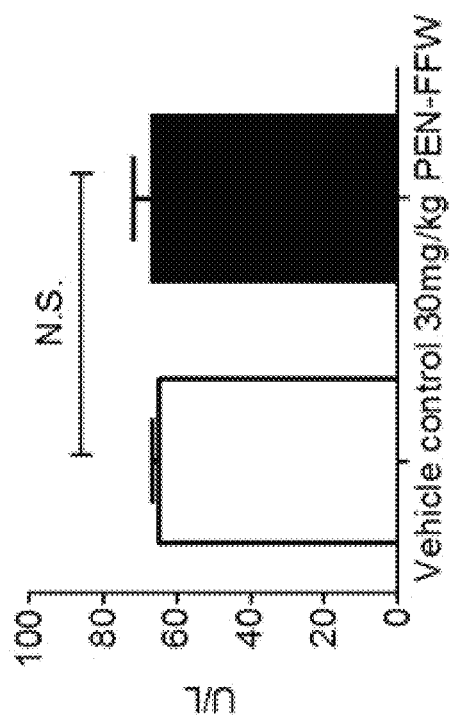
FIG. 11B
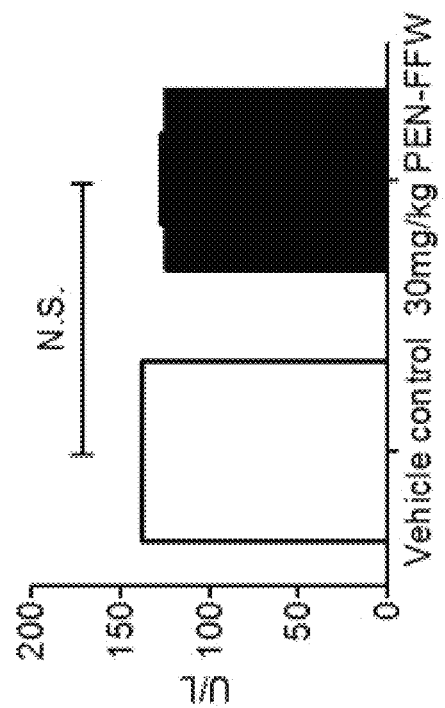

|  | Vehicle Control | PEN-FFW |
| --- | --- | --- |
| WBC ($10^3/\mu L$) | 11.9 ± 3.15 | 6.8 ± 1.5 |
| RBC ($10^6/\mu L$) | 11.0 ± 0.5 | 9.7 ± 0.2 |
| HGB (g/dL) | 16.85 ± 0.6 | 14.9 ± 0.3 |
| HCT (%) | 51.1 ± 2.5 | 45.9 ± 0.3 |
| MCV (fL) | 46.4 ± 0.2 | 47.0 ± 0.8 |
| PCT (%) | 0.26 ± 0.07 | 0.06 ± 0.02 |

WBC = White Blood Cell; RBC = Red Blood Cell; HGB = Haemoglobin; HCT = Haematocrit; MCV = Mean Corpuscular Volume; PCT = Procalcitonin

THERAPEUTIC SPALT-LIKE TRANSCRIPTION FACTOR 4 (SALL4) PEPTIDE

RELATED APPLICATION

This application is the U.S. National Stage of International Application No. PCT/US2017/030164, filed Apr. 28, 2017, which designates the U.S., published in English, and claims the benefit of U.S. Provisional Application No. 62/329,010, filed on Apr. 28, 2016. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 44591138002_SUBSTITUTESEQUENCE-LISTING; created May 11, 2020, 20 KB in size.

BACKGROUND OF THE INVENTION

Spalt-Like Transcription Factor 4 (SALL4) plays an essential role in developmental events and the maintenance of stem cell pluripotency. SALL4 is a zinc finger transcription factor, that forms a core transcriptional network with POU5FI (Oct4), Nanog and Sox2, which activates genes related to proliferation in embryonic stem cells (ESCs). SALL4 binds to retinoblastoma binding protein 4 (RBBp4), a subunit of the nucleosome remodeling and histone deacetylation (NuRD) complex and the SALL4 bound complex is recruited to various downstream targets including transcription factors. Beside the NuRD complex, SALL4 is also reported to bind to other epigenetic modifiers, altering gene expression. The binding of SALL4 to NuRD complex allows SALL4 to act as a transcriptional repressor for various downstream targets. An example of such downstream target includes, but is not limited to Phosphatase and Tensin homolog (PTEN), a factor that is essential for the self-renewal of leukemic stem cells (LSCs).

SALL4 is a viable potential target, as it is aberrantly expressed in various conditions or diseased states including solid tumors and other hematological tumors. Over the past few years, much effort has been expended to develop peptide based anti-cancer drugs. A major limitation of such peptide based therapies is the lack of target specificity. It is difficult to target a peptide to a particular tissue or cell without having the information on specific binding pockets or specific interaction sites on the surface molecules (e.g., receptors) of the cell or tissue that is to be targeted.

Accordingly, there is a need for compositions of improved peptide based drugs, particularly for the treatment of solid and hematological tumors. There is also a need for methods for using such compositions.

SUMMARY OF THE INVENTION

Described herein are isolated peptides that target the SALL4-RBBp4 interaction. SALL4 has been proposed to be a viable target for certain diseases (e.g., cancers) due to its selective expression in these diseases. However SALL4 falls into a class of so-called undruggable targets, as it lacks a typical, druggable pocket for inhibitor binding. The crystal structure of SALL4-RBBp4 complex was recently determined, leading to the identification of the site of key interactions between the two proteins. Based on the structure-function studies, it was shown herein that isolated peptides that block the SALL4-RBBp4 interaction have therapeutic value in various diseases with cells expressing SALL4. For instance, many solid tumors have aberrant SALL4 expression while normal tissues do not express SALL4.

Accordingly, in one aspect, the invention is directed to isolated peptides that inhibit the binding of SALL4 with RBBp4. The present invention provides isolated peptides that bind to RBBp4 protein such that the isolated peptides compete with the binding of the WT SALL4 peptide for the same site in the RBBp4 protein. In one embodiment, the isolated peptides described in this invention have a higher binding affinity for RBBp4 than the WT SALL4 peptide.

In another aspect, the invention is directed to pharmaceutical compositions comprising isolated peptides of the current invention. These compositions can be used for various applications, for instance, for the treatment of hepatocellular carcinoma.

In yet another aspect, the invention is directed to a method of inhibiting the binding of SALL4 with RBBp4 by contacting the cells expressing SALL4 with at least one of the isolated peptides described herein.

In another aspect, the invention is directed to a method of treating a disorder mediated by a dysregulation of SALL4 or NuRD. In yet another aspect, the invention is directed to a method of treating a disorder mediated by a dysregulation of phosphor AKT, CCND2, OCT4, ZNHIT6, WKN1 or SNHG12. This method comprises administering a therapeutically effective amount of the pharmaceutical composition to a subject in need thereof.

As a stem cell factor implicated in normal development, SALL4 is not expressed in most of the adult tissues but expressed in various diseased tissues. The isolated peptides targeting SALL4 are thus very selective; overcoming the biggest hurdle of selective targeting for peptide based therapeutic agents. Specificity is one of the important criteria for any therapeutic peptide, as the more specific the peptide is, the fewer side effects it brings about. Hence, the isolated peptides, pharmaceutical compositions and methods described herein have certain advantageous properties that are useful in multiple therapeutic and non-therapeutic applications.

BRIEF DESCRIPTION OF THE DRAWINGS

U.S. Provisional Application No. 62/329,010 ('010 Application), filed on Apr. 28, 2016 contains color drawings which correspond to drawings in the instant application. With regard to indications of color within the instant description of the figures provided herein, reference is made to those corresponding drawings and associated descriptions of the '010 Application.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A shows an Isothermal Calorimetric Assay (ITC) profile of WT SALL4 peptide titrated against RBBp4 are shown in raw (upper panel) and simulated curve in 1:1 binding model (lower panel). FIG. 1B is a sensogram of surface plasmon resonance demonstrated binding of WT SALL4 peptide to RBBp4 immobilised on a dextran coated chip.

FIG. 2A shows a front view of SALL4-RBBp4 complex. RBBp4 is depicted in yellow, green (beta sheet), and red (alpha helix), and the SALL4 peptide is depicted in blue. N and C terminals of RBBp4 are labelled. FIG. 2B shows electrostatic potential represented by red (acidic patches), white (neutral) and blue (basic). OR Diagram representing electrostatic potential. Acidic patches are indicated in red, neutral in white and basic in blue. FIG. 2C shows the final $2F_0-F_c$ electron density map (contoured at $1\sigma$) for the key residues of SALL4 peptide from Met1 to Ile 12. FIG. 2D shows side-chains of RBBP4 (green) interacting with SALL4 peptide (blue) is shown in stick representation. Unique interactions of SALL4-RBBp4 are shown in the boxes. All structure-related figures in this paper were prepared using the program PyMol.

FIG. 3A shows computational alanine scanning (CAS) carried out on all 12 residues of the SALL4 peptide. The difference in the binding free energy ($\Delta\Delta G_{bind}$) of the alanine mutants ($\Delta G_{mutant}$, Ala7 was mutated to glycine) and wild type ($\Delta G_{wild\ type}$) was calculated ($\Delta\Delta G_{bind} = \Delta G_{mutant} - \Delta G_{wild\ type}$). $\Delta\Delta G_{bind}$ was tabulated (left) and plotted in a bar chart (right). FIG. 3B shows alignment of mutant peptides. Mutated residues are highlighted in red. The $IC_{50}$ of each peptide, including WT, was determined by Fluorescence Polarization (FP). Different concentrations of each peptide were titrated into a mixture of 0.04 µM RBBp4 and 0.01 µM of C-labelled FITC-SALL4 WT peptide. Polarization was measured in mP. FIG. 3C shows representative $IC_{50}$ curves of SALL4 WT and double mutant 3,5A by FP. FIG. 3D shows cell viability assays performed on SNU398 cells treated with SALL4 WT or mutant 3,5A peptides. Pep-1 carrier was added to the peptide to facilitate cellular penetration of the peptides. FIG. 3E shows transcript levels of SALL4-RBBp4 downstream gene, PTEN, were measured using quantitative real-time PCR.

FIG. 4A shows computational modelling of FFW (SEQ ID NO: 14) and WT SALL4 (SEQ ID NO: 13) peptide binding to RBBp4. FIG. 4B shows a fluorescence polarization assay of FFW as compared with the original 12-residue SALL4 WT peptide ($IC_{50}$=0.023 vs. 1.30 µM).

FIG. 5A shows the Penetratin sequence (SEQ ID NO: 2) was added to WT (SEQ ID NO: 13), MUT (SEQ ID NO: 39), and FFW (SEQ ID NO: 14) peptides to aid cellular penetration. FIG. 5B shows Penetratin-conjugated peptides, subjected to the cell viability assay in SNU398 cells, demonstrating the high potency of PEN-FFW.

FIG. 6A: Peptides were added to HCC cell line SNU398 with high expression of SALL4. FIG. 6B: HCC cell line SNU387 with no expression of SALL4, and cell viability was measured after 72 hr of incubation.

FIG. 7A: $7.2\times10^5$ SNU398 cells were inoculated subcutaneously into the right flank of NOD/SCID/gamma mice (NSG mice). Tumors were allowed to grow for one week before peptide treatments were administered every alternate day for a total of five injections. FIG. 7B: Tumor growth was documented by plotting tumor volume against time. Mice administrated with PEN-FFW had a significant reduced growth rate of HCC xenograft when compared to PEN (P=0.0008), PEN-MUT (P=0.001), and PEN-WT (P=0.01). FIG. 7C: Relative size of tumors resected on day 20. FIG. 7D: tumor weight was determined (n=5). PEN-FFW treated mice had the smallest tumors (µ=88.34 mg) compared to PEN (µ=1550.78 mg), PEN-MUT (µ=1273.46 mg) and PEN-WT (µ=563.46 mg). FIG. 7E: Total RNA was isolated from the resected tumors and expression of PTEN was measured using real-time PCR.

FIGS. 9A-9E. Clinical significance of PEN-FFW compared to Sorafenib. FIG. 9A: PEN-FFW treated SNU398 tumor xenografts were compared to that of Sorafenib treated xenografts. FIG. 9B: PEN-FFW treated PLC8024 tumor xenografts were compared to that of Sorafenib treated xenografts. Mice body weight was measured to access toxicity of various peptides. FIG. 9C: Body weight of mice at day 17. FIG. 9D: Differences of body weight compared to day 0 (As indicated by the arrow in far left of FIG. 7A). FIG. 9E: Body weight of mice at day 19th in the experiment shown in FIG. 9A comparing effect of Sorafenib and PEN-FFW. Data represent mean±s.d. (n=5).

FIG. 10A: Degradation profile of PEN-FFW monitored by LC-MS/MS for upto 24 hours. Inset of FIG. 10A shows that PEN-FFW was found to be stable to plasma proteases with more than 90% of the peptide remaining in the plasma after 30 min. FIG. 10B: Degradation profile of Eucatropine as the control monitored by LC-MS/MS for upto 1500 minutes showed that Eucatropine was rapidly degraded. Inset of FIG. 10B shows that Eucatropine was rapidly degraded to 40% within 30 min. FIG. 10C: Live cell imaging of SNU398 cells treated with a N-terminal FITC conjugated PEN-FFW. Live cell imaging was performed on these cells at 2 min interval for the first one hour, and at 5 min interval for the subsequent 23 hr to assess the permeability and stability of FITC-PEN-FFW.

FIGS. 11A-11D Toxicity of PEN-FFW in C57BL/6 mice (n=4). Mice were exposed to intraperitoneal (IP) administration of PEN-FFW (30 mg/kg) or vehicle (10% DMSO) every alternate day over the course of 17 days to a cumulative dose of 270 mg/kg. FIG. 11A: Traced body weight or end point body weight of the mice were shown. These mice did not exhibit notable signs of toxicity such as weight loss, lethargy or loss of mobility. FIG. 11B: Serum AST and ALT of the mice were measured with no significant change of the two groups. FIG. 11C: Blood count of these mice were measured and no significant change was observed in the blood count. FIG. 11D: Representative microphotographs of tissue sections from the major organs (heart, liver, lung, spleen stomach) harvested from vehicle control and PEN-FFW treated animals. No tissue damage was observed by microscopic examination.

FIG. 12A: Kaplan Meier survival analysis with TCGA HCC patient RNA-seq data set was performed using individual genes from the 9-gene subset from PEN-FFW DEGs. Predictive power of six individual DEGs are shown as indicated by the "P" value in the figure. FIG. 12B: Example of Combinatorial study with the PEN-FFW DEGs that have no predictive power individually. When used as single gene, these DEGs has no statistical power in predicting patient outcome as shown in the left and the middle panels. However, when used in combination, significant low Hazard ratio was observed as shown in the right panel.

DETAILED DESCRIPTION OF THE INVENTION

Figures 1A, 1B:
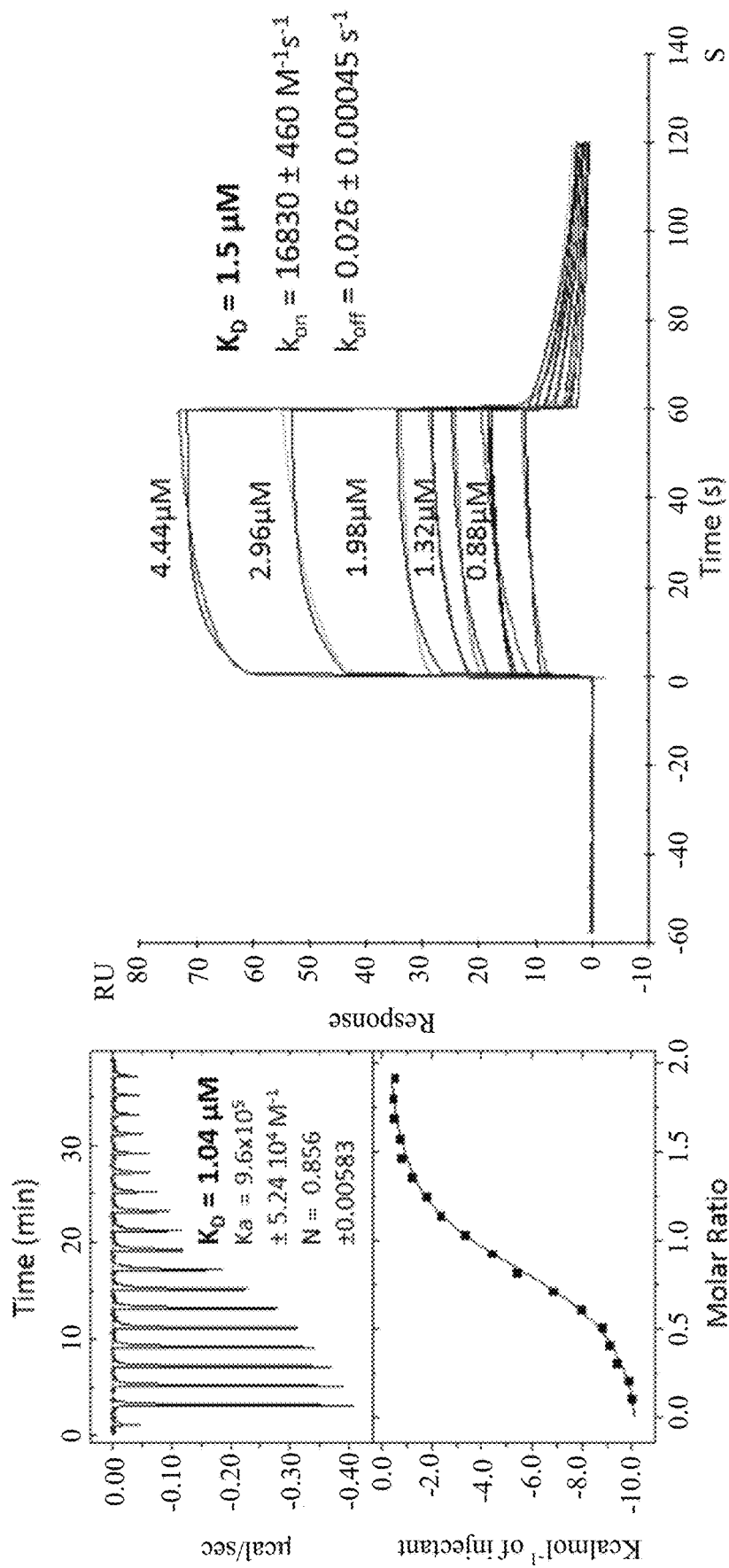
FIGS. 1A-1B. Binding affinity of WT SALL4 (1-12 aa) to RBBp4.

Isolated Peptides and Compositions Comprising Isolated Peptides

The present invention relates to isolated peptides comprising amino acids that are selected based on structure-function studies by the inventors on the interaction of a fragment of the human Spalt-Like Transcription Factor 4 (SALL4) with retinoblastoma binding protein 4 (RBBp4). The term "peptide" as used herein, refers to a compound having two or more amino acids linked in a chain, the carboxyl group of each acid being joined to the amino group of the next by a bond of the type —OC—NH—. A "peptide" is commonly known to those of skill in the art.

The present invention, in certain embodiments, provides isolated peptides comprising an amino acid sequence set forth in formula (I):

$$RRKX_1X_2X_3X_4X_5X_6X_7, \quad (I)$$

The sequence of amino acids in formula (I) follows the standard convention for representing amino acid sequences of peptides. Amino acids in formula (I) are written from the N-terminus (on the left) to the C-terminus (on the right). All the formulae and the sequences mentioned in this application and in its sequence listing, follow the same convention. Amino acid residues in formula (I) are represented by single-letter symbols that are well known to a person skilled in the art. For example, the single letter codes used in formula (I) have the following meaning: R=Arg=arginine, K=Lys=lysine. Amino acids $X_1$, $X_2$, $X_3$, $X_4$, $X_5$, $X_5$, $X_6$, or $X_7$ in formula (I) independently refer to an amino acid with a non-polar side chain, a polar side chain that is not charged at neutral pH or a polar side chain that is positively charged at neutral pH. The expression "non-polar side chain" as used herein, refers to a side chain "R" group of a naturally occurring or unnatural amino acid that is uncharged at physiological pH and cannot form or participate in a hydrogen bond. Examples of amino acids with a non-polar side chain include, but not limited to, glycine (Gly), alanine (Ala), valine (Val), leucine (Leu), isoleucine (Ile), proline (Pro), phenylalanine (Phe), methionine (Met), and norleucine (Nle). Tryptophan (Trp) is a non-polar amino acid that is an exception due the presence of a hydrogen donor atom in its side chain. An amino acid with "non-polar side chain" is commonly known to those of skill in the art. The expression "polar side chain that is not charged at neutral pH" as used herein, refers to a side chain "R" group of a naturally occurring or unnatural amino acid that is substantially uncharged at physiological pH and has hydrogen donor or acceptor atoms in its side chain that can participate in a hydrogen bond. Examples of amino acids with a polar side chain that is substantially uncharged at neutral pH include, but not limited to, serine (Ser), threonine (Thr), cysteine (Cys), asparagine (Asn), glutamine (Gln), and tyrosine (Tyr). An amino acid with "polar side chain that is not charged at neutral pH" is commonly known to those of skill in the art. The expression "polar side chain that is charged at neutral pH" as used herein, refers to a side chain "R" group of a naturally or unnaturally occurring amino acid that is substantially charged at physiological pH and can participate in hydrogen bonding as it has hydrogen donor or acceptor atoms in its side chain. Examples of amino acids with a polar side chain that is substantially charged at physiological pH include, but not limited to, arginine (Arg), lysine (Lys), ornithine (Orn) and histidine (His), aspartic acid or aspartate (Asp) and glutamic acid or glutamate (Glu). An amino acid with a "polar side chain that is charged at neutral pH" is commonly known to those of skill in the art. The term "substantially" as used herein means "for the most part" or "predominantly" or "at least partially". For example, glutamic acid is considered to be negatively charged at neutral pH as the carboxylic side chain loses an H+ ion (proton). In reality there exists an equilibrium between the negatively charged un-protonated form and the uncharged protonated form of glutamic acid in a peptide. Glutamic acid is considered to have a "substantial" negative charge at neutral pH because the equilibrium is shifted towards the un-protonated form and the "predominant" species in solution is the negatively charged species. In certain embodiments, $X_1$ is an amino acid with a non-polar aromatic side chain. In certain embodiments, $X_2$ is an amino acid with a polar side chain that has a substantial positive charge at neutral pH. In certain embodiments, $X_3$ is an amino acid with a non-polar side chain, or a polar side chain that has a substantial positive charge at neutral pH. In certain embodiments, $X_4$ is an amino acid with a non-polar side chain. In certain embodiments, $X_5$ is an amino acid with a non-polar side chain, a polar side chain that is not charged at neutral pH, a polar side chain that has a substantial negative charge at neutral pH. In certain embodiments, $X_6$ is an amino acid with a non-polar side chain. In certain embodiments, $X_7$ is an amino acid with a non-polar side chain. In certain embodiments, $X_1$ is an amino acid with a non-polar aromatic side chain; $X_2$ is an amino acid with a polar side chain that has a substantial positive charge at neutral pH; $X_3$ is an amino acid with a non-polar side chain, or a polar side chain that has a substantial positive charge at neutral pH; $X_4$ is an amino acid with a non-polar side chain; $X_5$ is an amino acid with a non-polar side chain, a polar side chain that is not charged at neutral pH, a polar side chain that has a substantial negative charge at neutral pH; $X_6$ is an amino acid with a non-polar side chain; and $X_7$ is an amino acid with a non-polar side chain. In some embodiments, the invention provides isolated peptides comprising an amino acid sequence set forth in formula (I), wherein one or more of amino acids $X_1$, $X_2$, $X_3$, $X_4$, $X_5$, $X_6$, or $X_7$ are optional. In some embodiments, formula (I) does not encompass the WT SALL4 peptide represented by the amino acid sequence MSRRKQAKPQHI (SEQ ID NO: 13). The term "unnatural amino acid" or the phrase "unnaturally occurring amino acid" refers to any amino acid, modified amino acid, and/or amino acid analogue that is not one of the 20 naturally occurring amino acids or seleno cysteine. For example unnatural amino acids include, but are not limited to, D-enantiomers of 20 naturally occurring amino acids, ornithine and beta-lysine. Physiological pH or neutral pH refers to a pH value of 7.0. Exemplary unnatural amino acids are shown below and should not be construed as limiting.

Leu and Ile analogs

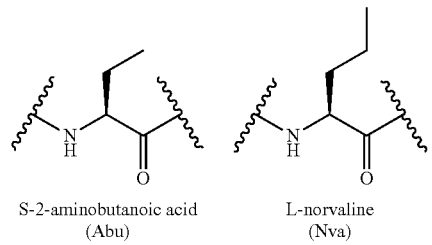

S-2-aminobutanoic acid (Abu)  L-norvaline (Nva)

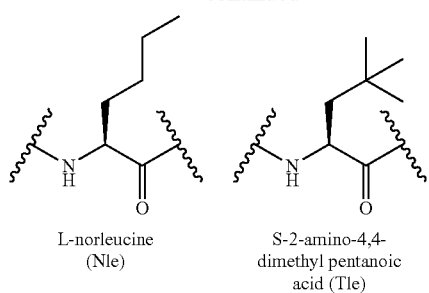

L-norleucine (Nle)

S-2-amino-4,4-dimethyl pentanoic acid (Tle)

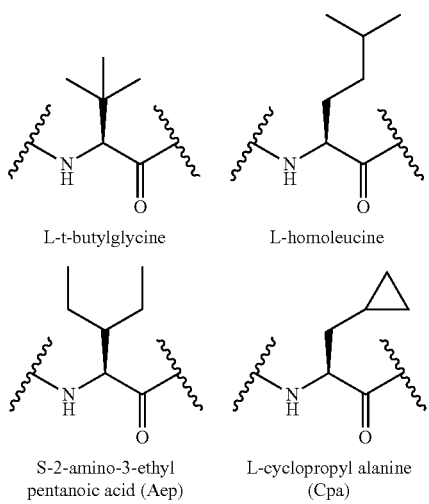

L-t-butylglycine

L-homoleucine

S-2-amino-3-ethyl pentanoic acid (Aep)

L-cyclopropyl alanine (Cpa)

L-cyclobuttyl alanine (Cbu)

L-cyclopentyl alanine (Cpe)

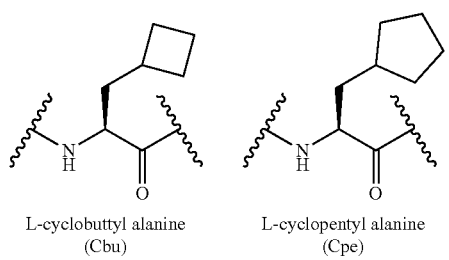

L-cyclohexyl alanine (Cha)

L-cycloheptyl alanine (Che)

Phe and Trp analogs

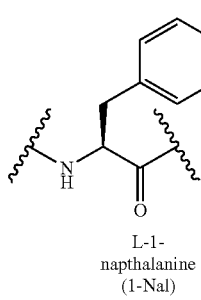

L-1-napthalanine (1-Nal)

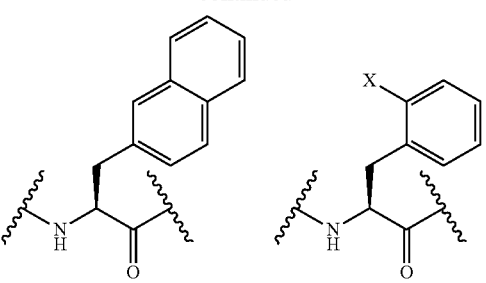

L-2-napthalanine (2-Nal)

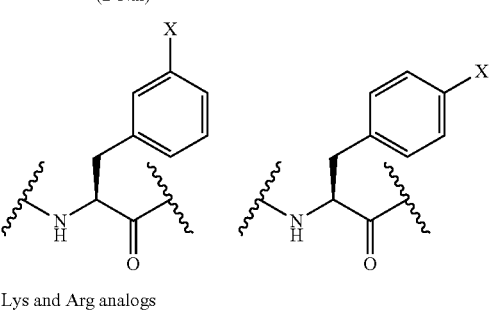

Lys and Arg analogs

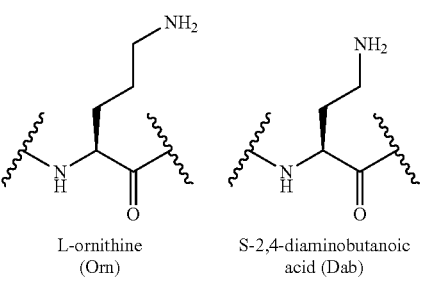

L-ornithine (Orn)

S-2,4-diaminobutanoic acid (Dab)

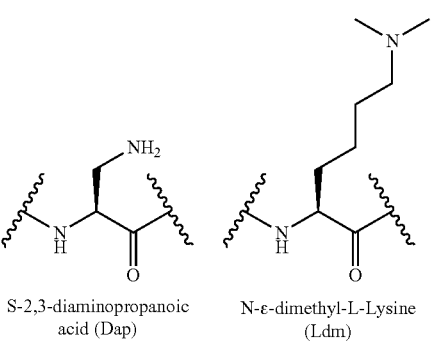

S-2,3-diaminopropanoic acid (Dap)

N-ε-dimethyl-L-Lysine (Ldm)

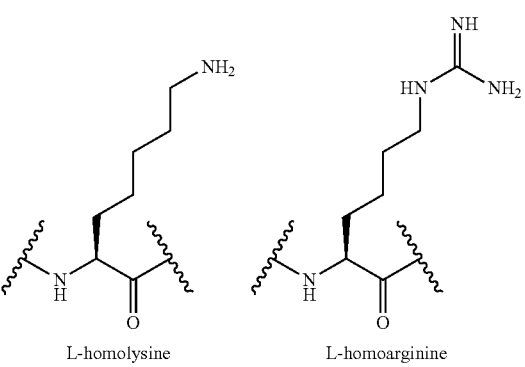

L-homolysine

L-homoarginine

-continued

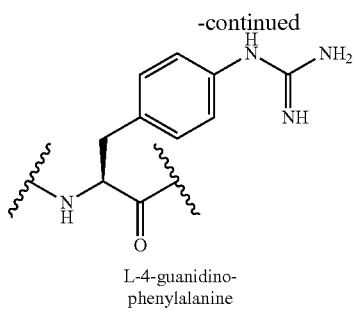

L-4-guanidino-
phenylalanine

X = amine, nitro, alcohol, ether, thioether, halogen, alkyl, acyl, phenyl

The present invention, in some embodiments, provides isolated peptides comprising an amino acid sequence set forth in formula (Ia):

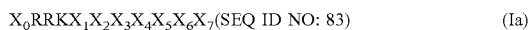

Amino acids $X_0$, $X_1$, $X_2$, $X_3$, $X_4$, $X_5$, $X_6$, or $X_7$ in formula (Ia) independently refer to an amino acid with a non-polar side chain, a polar side chain that is not charged at neutral pH or a polar side chain that is positively charged at neutral pH. In certain embodiments, $X_0$ is an amino acid with a non-polar side chain or a polar side chain that has a substantial positive charge at neutral pH. For example, $X_0$ can be amino acid represented by the single letter code which has the following meaning: O=Orn=Ornithine, Z=Glx=Glutamic Acid or Glutamine, U=Sec=Selenocysteine. In certain embodiments, $X_1$ is an amino acid with a non-polar aromatic side chain. In certain embodiments, $X_2$ is an amino acid with a polar side chain that has a substantial positive charge at neutral pH. In certain embodiments, $X_3$ is an amino acid with a non-polar side chain, or a polar side chain that has a substantial positive charge at neutral pH. In certain embodiments, $X_4$ is an amino acid with a non-polar side chain. In certain embodiments, $X_5$ is an amino acid with a non-polar side chain, a polar side chain that is not charged at neutral pH, a polar side chain that has a substantial negative charge at neutral pH. In certain embodiments, $X_6$ is an amino acid with a non-polar side chain. In certain embodiments, $X_7$ is an amino acid with a non-polar side chain. In certain embodiments, $X_0$ is an amino acid with a non-polar side chain or a polar side chain that has a substantial positive charge at neutral; $X_1$ is an amino acid with a non-polar aromatic side chain; $X_2$ is an amino acid with a polar side chain that has a substantial positive charge at neutral pH; $X_3$ is an amino acid with a non-polar side chain, or a polar side chain that has a substantial positive charge at neutral pH; $X_4$ is an amino acid with a non-polar side chain; $X_5$ is an amino acid with a non-polar side chain, a polar side chain that is not charged at neutral pH, a polar side chain that has a substantial negative charge at neutral pH; $X_6$ is an amino acid with a non-polar side chain; and $X_7$ is an amino acid with a non-polar side chain. In some embodiments, the invention provides isolated peptides comprising an amino acid sequence set forth in formula (Ia), wherein one or more of amino acids $X_0$, $X_1$, $X_2$, $X_3$, $X_4$, $X_5$, $X_6$, or $X_7$ are optional.

In some embodiments, the present invention provides isolated peptides comprising an amino acid sequence set forth in formula (II):

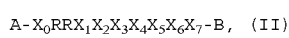

Amino acids $X_0$, $X_1$, $X_2$, $X_3$, $X_4$, $X_5$, $X_6$, or $X_7$ in formula (II) independently refer to an amino acid with a non-polar side chain, a polar side chain that is not charged at neutral pH or a polar side chain that is positively charged at neutral pH. In certain embodiments, $X_0$ is an amino acid with a non-polar side chain or a polar side chain that has a substantial positive charge at neutral pH. For example, $X_0$ can be amino acid represented by the single letter code which has the following meaning: O=Orn=Ornithine, Z=Glx=Glutamic Acid or Glutamine, U=Sec=Selenocysteine. In certain embodiments, $X_1$ is an amino acid with a non-polar aromatic side chain. In certain embodiments, $X_2$ is an amino acid with a polar side chain that has a substantial positive charge at neutral pH. In certain embodiments, $X_3$ is an amino acid with a non-polar side chain, or a polar side chain that has a substantial positive charge at neutral pH. In certain embodiments, $X_4$ is an amino acid with a non-polar side chain. In certain embodiments, $X_5$ is an amino acid with a non-polar side chain, a polar side chain that is not charged at neutral pH, a polar side chain that has a substantial negative charge at neutral pH. In certain embodiments, $X_6$ is an amino acid with a non-polar side chain. In certain embodiments, $X_7$ is an amino acid with a non-polar side chain. In certain embodiments, $X_0$ is an amino acid with a non-polar side chain or a polar side chain that has a substantial positive charge at neutral; $X_1$ is an amino acid with a non-polar aromatic side chain; $X_2$ is an amino acid with a polar side chain that has a substantial positive charge at neutral pH; $X_3$ is an amino acid with a non-polar side chain, or a polar side chain that has a substantial positive charge at neutral pH; $X_4$ is an amino acid with a non-polar side chain; $X_5$ is an amino acid with a non-polar side chain, a polar side chain that is not charged at neutral pH, a polar side chain that has a substantial negative charge at neutral pH; $X_6$ is an amino acid with a non-polar side chain; and $X_7$ is an amino acid with a non-polar side chain. In some embodiments, the invention provides isolated peptides comprising an amino acid sequence set forth in formula (II), wherein one or more of amino acids $X_0$, $X_1$, $X_2$, $X_3$, $X_4$, $X_5$, $X_6$, or $X_7$ are optional. In some embodiments, formula (II) does not encompass the WT SALL4 peptide represented by the amino acid sequence MSRRKQAKPQHI (SEQ ID NO: 13).

"A" in formula (II) is an acetyl group or an N-terminal protecting group covalently bonded to the α-amino group of $X_0$. As used herein, "N-terminal protecting group" refers to those groups intended to, e.g., block, protect, and/or modify the physical, chemical, and/or biological properties of the α-N-terminal of an amino acid or peptide or to otherwise protect the amino group of an amino acid or peptide against undesirable reactions during synthetic procedures. Commonly used N-protecting groups are disclosed in Greene, "Protective Groups In Organic Synthesis," (John Wiley & Sons, New York (1981)), which is hereby incorporated by reference. Representative N-terminal protecting groups are C1-C8 lower alkanoyl (e.g., acetyl, propionyl, pivaloyl, t-butylacetyl and the like). Additionally, protecting groups can be used as pro-drugs which are readily cleaved in vivo, for example, by enzymatic hydrolysis, to release the biologically active parent. α-N-terminal protecting groups comprise C1-C8 lower alkanoyl groups such as formyl, acetyl ("Ac"), propionyl, pivaloyl, t-butylacetyl and the like; other C1-C8 acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like.

"B" in formula (II) is an amine group or a C-terminal protecting group covalently bonded to the terminal carbonyl of $X_7$. "C-terminal protecting group" or as the term "carboxy protecting group" refers to a carboxylic acid protecting group, such as an ester or an amide group employed to, e.g., block, protect, and/or modify the physical, chemical, and/or biological properties of the carboxylic acid moiety. Carboxylic acid (or carboxy) protecting groups are disclosed in Greene, "Protective Groups in Organic Synthesis" pp. 152-186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are C1-C8 lower alkyl (e.g., methyl, ethyl or t-butyl and the like); aryl-(C1-C8)-alkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-((C1-C8) loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like. For example, "B" in formula (II) can be an ester or amide that is formed by reaction of the "C-terminal protecting group" with the terminal carboxyl group of amino acid $X_7$.

In the first embodiment, the invention provides peptides comprising the sequence: RRKX$_1$AKPQHI (SEQ ID NO: 4), wherein $X_1$ is an amino acid with a non-polar aromatic side chain. The second embodiment of the invention provides peptides comprising the sequence: RRKQX$_2$KPQHI (SEQ ID NO: 5), wherein $X_2$ is an amino acid with a polar side chain that is positively charged at neutral pH. In the third embodiment, the invention provides peptides comprising the sequence: RRKQAX$_3$PQHI (SEQ ID NO: 6), wherein $X_3$ is an amino acid with a non-polar side chain, or a polar side chain that is positively charged at neutral pH, or both. In the fourth embodiment, the invention provides peptides comprising the sequence: RRKQAKX$_4$QHI (SEQ ID NO: 7), wherein $X_4$ is an amino acid with a non-polar side chain. The fifth embodiment of the invention provides peptides comprising the sequence: RRKQAKPX$_5$HI (SEQ ID NO: 8) wherein $X_5$ is an amino acid with a non-polar side chain, a polar side chain that is not charged at neutral pH, a polar side chain that is negatively charged at neutral pH or a combination thereof. In the sixth embodiment, the invention provides peptides comprising the sequence: RRKQAKPQX$_6$I (SEQ ID NO: 9) wherein $X_6$ is an amino acid with a non-polar side chain. In the seventh embodiment, the invention provides peptides comprising the sequence: RRKQAKPQHX$_7$ (SEQ ID NO: 10), wherein $X_7$ is an amino acid with a non-polar side chain. In the eighth embodiment, the invention provides peptides comprising the sequence: RRKX$_1$AKX$_4$QX$_6$I (SEQ ID NO: 11), wherein $X_1$, $X_4$ or $X_6$ is independently selected from amino acids with non-polar side chains. The ninth embodiment of the invention provides peptides comprising the sequence: X$_0$RRKQAKPQHI (SEQ ID No. 12), wherein $X_0$ is an amino acid with a non-polar side chain or a polar side chain that is positively charged at neutral pH. The tenth embodiment of the invention provides peptides that can be any one of the sequence wherein the peptide is RRKQAKPQHI (SEQ ID NO: 3), RRKAAKPQHI (SEQ ID NO: 15), RRKFAKPQHI (SEQ ID NO: 16), RRKQKKPQHI (SEQ ID NO: 17), RRKQRKPQHI (SEQ ID NO: 18), RRKQAAPQHI (SEQ ID NO: 19), RRKQAVPQHI (SEQ ID NO: 20), RRKQALPQHI (SEQ ID NO: 21), RRKQAFPQHI (SEQ ID NO: 22), RRKQARPQHI (SEQ ID NO: 23), RRKQAKFQHI (SEQ ID NO: 24), RRKQAKPAHI (SEQ ID NO: 25), RRKQAKPEHI (SEQ ID NO: 26), RRKQAKPNHI (SEQ ID NO: 27), RRKQAKPVHI (SEQ ID NO: 28), RRKQAKPLHI (SEQ ID NO: 29), RRKQAKPQAI (SEQ ID NO: 30), RRKQAKPQFI (SEQ ID NO: 31), RRKQAKPQYI (SEQ ID NO: 32), RRKQAKPQWI (SEQ ID NO: 33), RRKQAKPQVI (SEQ ID NO: 34), RRKQAKPQHA (SEQ ID NO: 35), RRKQAKPQHV (SEQ ID NO: 36), RRKQAKPQHL (SEQ ID NO: 37), RRKQAKPQHF (SEQ ID NO: 38), RRKFAKFQWI (SEQ ID NO: 14), RRKHAKPQHI (SEQ ID NO: 40), ORRKQAKPQHI (SEQ ID NO: 41), HRRKQAKPQHI (SEQ ID NO: 42), RRKQPKPQHI (SEQ ID NO: 43), HRRKQAKPQHI (SEQ ID NO: 44), URRKQAKPQHI (SEQ ID NO: 45) or ZRRKQAKPQHI (SEQ ID NO: 46).

In all the embodiments described above, the terminal ends may be free or protected such that the amino and the carboxy terminals of the peptides protected as described above. The protection can be through an "N-terminal protecting group" or a "C-terminal protecting group" or both, with or without additional cell penetrating sequence. In some embodiments, the peptides having amino acid sequences provided in the tenth embodiment above are protected by an acetyl group on the N-terminus. In some other embodiments, the peptides having amino acid sequences provided in the tenth embodiment above are protected by an amine group on the C-terminus. In certain embodiments, the peptides having amino acid sequences provided in the tenth embodiment above are protected by the reaction of the terminal carboxyl group of the peptide with a "C-terminal protecting group" to form an ester or an amide group. In further embodiments, the peptides having amino acid sequences provided in the tenth embodiment above are protected by an acyl group on the N-terminus and an amine on the C-terminus.

In a further embodiment, the invention provides isolated peptides of the present invention further comprising a cell-penetrating peptide. "Cell-penetrating peptide" or "CPP" or "peptide carrier" as used herein, refers to any short peptide that can penetrate or cross the cell membrane of live cells. These short peptides can penetrate the cell membrane either by themselves or when they are attached to other peptides. In the present text, CPP, is a molecule, the core of which is a peptide. Other chemical groups can however be covalently bound to said peptidic core, in order to improve the overall stability of the molecule, and/or to provide it with additional properties, such as targeting ability. For example, a cell-penetrating peptide according to the invention can comprise any one of the isolated peptides described in this invention, covalently linked to the C-terminal extremity of the cell penetrating peptide. In some embodiments the isolated peptide of the current invention is covalently linked to the N-terminal extremity of the cell penetrating peptide. In some embodiments, the peptides having amino acid sequences provided in the tenth embodiment above are covalently linked to the C or the N-terminal extremity of the cell penetrating peptide. In a particular embodiment, any one of the peptides having amino acid sequences provided in the tenth embodiment is covalently linked to the C-terminal extremity of the cell penetrating peptide comprising an amino acid sequence set forth in RQIKIWFQNRRMKWKK (SEQ ID NO: 2). Other peptides that are functional equivalents or homologues that mimic the function of peptide in SEQ ID NO: 2 can also be used as a cell penetrating peptide by covalently linking to any one of the isolated peptides of the current invention. The term "covalently linked", as used herein, refers to any interaction by any attractive force between atoms strong enough to allow the combined aggregate to function as a unit. This includes, but is not limited to, chemical bonds such as covalent bonds (for example, polar, or nonpolar), and non-covalent bonds such as ionic bonds, metallic bonds, and/or bridge bonds. Methods of covalently linking a cell penetrating peptide with other isolated peptides, types of covalent linkages between a cell penetrating peptide and an isolated peptide are routinely used in the field of the current invention and are also well known to one of skill in the art (*Drug Discovery Today*. Vol 17. Numbers 15/16, 850-860, August 2102).

The present invention provides isolated peptides that bind to RBBp4 protein such that the isolated peptides compete with the binding of the WT SALL4 peptide for the same site in the RBBp4 protein. Accordingly, in one embodiment, the invention provides isolated peptides that have a binding affinity higher than the binding affinity of the WT SALL4 peptide represented by the amino acid sequence MSRRKQAKPQHI (SEQ ID NO: 13). In one particular embodiment, the invention provides isolated peptides with a binding affinity that is at least 2 fold higher than the WT SALL4 peptide represented by the amino acid sequence MSRRKQAKPQHI (SEQ ID NO: 13). In a different embodiment, the isolated peptides of the current invention have a binding affinity that is at least 3-fold higher than the WT SALL4 peptide in SEQ ID NO: 13. The term, "binding affinity", as used herein, refers to a measure of the strength and/or the specificity of interaction between any two peptides. Frequently, binding affinity is represented in terms of dissociation constant ($K_D$). For example, a high affinity interaction between two peptides generally has a lower $K_D$ value, typically in the sub micromolar to picomolar range. Alternatively, binding affinity is also frequently reported as $IC_{50}$ values. The "$IC_{50}$ value", as used in the present invention, refers to the half maximal inhibitory concentration at which the binding of the test peptide with the RBBp4 protein results in the inhibition of growth of a cell expressing SALL4. "Binding affinity" can be measured by any method known to a person of skill in the art including, but not limited to Fluorescence Polarization (FP) assay, Isothermal calorimetric (ITC) assay and surface plasmon resonance (SPR or Biacore). The terms "binding affinity", "dissociation constant" and "$IC_{50}$ value" are all used herein in the same meaning known to one of skill in the art. Binding affinity data for the isolated peptides described in this invention are shown below in Table 1.

TABLE 1

| Peptide | Sequence | NO: of residues | $IC_{50}$ (µM) |
|---|---|---|---|
| 1 | Ac-MSRRKQAKPQHI-NH2 | 12 | 1.04 ± 0.2 |
| *Truncation* | | | |
| 2 | Ac-MSRRKQAKPQH-NH2 | 11 | 1.29 ± 0.1 |
| 3 | Ac-MSRRKQAKPQ-NH2 | 10 | 0.80 ± 0.1 |
| 4 | Ac-MSRRKQAKP-NH2 | 9 | 1.91 ± 0.1 |
| 5 | Ac-SRRKQAKPQHI-NH2 | 11 | 0.60 ± 0.1 |
| 6 | Ac-RRRQAKPQHI-NH2 | 10 | 0.36 ± 0.1 |
| 7 | Ac-RKQAKPQHI-NH2 | 9 | >20 |
| *Ala scan peptide 6* | | | |
| 8 | Ac-ARKQAKPQHI-NH2 | 10 | >20 |
| 9 | Ac-RAKQAKPQHI-NH2 | 10 | >20 |
| 10 | Ac-RRAQAKPQHI-NH2 | 10 | >20 |
| 11 | Ac-RRKAAKPQHI-NH2 | 10 | 0.19 ± 0.01 |
| 12 | Ac-RRKQAAPQHI-NH2 | 10 | 0.16 ± 0.02 |
| 13 | Ac-RRKQAKAQHI-NH2 | 10 | 0.27 ± 0.03 |
| 14 | Ac-RRKQAKPAHI-NH2 | 10 | 0.12 ± 0.01 |
| 15 | Ac-RRKQAKPQAI-NH2 | 10 | 0.73 ± 0.2 |
| 16 | Ac-RRKQAKPQHA-NH2 | 10 | 0.46 ± 0.2 |
| *R1 mutation* | | | |
| 17 | Ac-KRKQAKPQHI-NH2 | 10 | 3.80 ± 0.5 |
| *R2 mutation* | | | |
| 18 | Ac-RKKQAKPQHI-NH2 | 10 | 2.30 ± 0.4 |
| *K3 mutation* | | | |
| 19 | Ac-RRRQAKPQHI-NH2 | 10 | 0.63 ± 0.2 |

TABLE 1 -continued

| Peptide | Sequence | NO: of residues | IC$_{50}$ (μM) |
|---|---|---|---|
| | Q4 mutation | | |
| 20 | Ac-RRKEAKPQHI-NH2 | 10 | 3.49 ± 0.5 |
| 21 | Ac-RRKNAKPQHI-NH2 | 10 | 0.92 ± 0.1 |
| 22 | Ac-RRKVAKPQHI-NH2 | 10 | 0.41 ± 0.1 |
| 23 | Ac-RRKLAKPQHI-NH2 | 10 | 0.27 ± 0.1 |
| 24 | Ac-RRKFAKPQHI-NH2 | 10 | |
| | A5 mutation | | |
| 25 | Ac-RRKQKKPQHI-NH2 | 10 | 0.38 ± 0.1 |
| 26 | Ac-RRKQRKPQHI-NH2 | 10 | 0.46 ± 0.1 |
| | K6 mutation | | |
| 27 | Ac-RRKQAVPQHI-NH2 | 10 | 0.91 ± 0.2 |
| 28 | Ac-RRKQALPQHI-NH2 | 10 | 0.31 ± 0.1 |
| 29 | Ac-RRKQAFPQHI-NH2 | 10 | 0.53 ± 0.1 |
| 30 | Ac-RRKQARPQHI-NH2 | 10 | 0.33 ± 0.1 |
| | P7 mutation | | |
| 31 | Ac-RRKQAKpQHI-NH2 | 10 | 6.60 ± 0.9 |
| 32 | Ac-RRKQAKVQHI-NH2 | 10 | 5.80 ± 0.8 |
| 33 | Ac-RRKQAKLQHI-NH2 | 10 | 4.40 ± 1.1 |
| 34 | Ac-RRKQAKFQHI-NH2 | 10 | 0.17 ± 0.03 |
| | Q8 mutation | | |
| 35 | Ac-RRKQAKPEHI-NH2 | 10 | 0.57 ± 0.1 |
| 36 | Ac-RRKQAKPNHI-NH2 | 10 | 0.79 ± 0.3 |
| 37 | Ac-RRKQAKPVHI-NH2 | 10 | 0.35 ± 0.1 |
| 38 | Ac-RRKQAKPLHI-NH2 | 10 | 0.46 ± 0.1 |
| | H9 mutation | | |
| 39 | Ac-RRKQAKPQFI-NH2 | 10 | 0.34 ± 0.07 |
| 40 | Ac-RRKQAKPQYI-NH2 | 10 | 2.85 ± 0.4 |
| 41 | Ac-RRKQAKPQWI-NH2 | 10 | 0.12 ± 0.03 |
| 42 | Ac-RRKQAKPQVI-NH2 | 10 | 0.48 ± 0.1 |
| | I10 mutation | | |
| 43 | Ac-RRKCIAKPQHV-NH2 | 10 | 0.84 ± 0.3 |
| 44 | Ac-RRKCIAKPOHL-NH2 | 10 | 0.59 ± 0.2 |
| 45 | Ac-RRKCIAKPQHF-NH2 | 10 | 0.64 ± 0.2 |
| | Final | | |
| 46 | Ac-RRKFAKFQWI-NH2 | 10 | 0.023 ± 0.003 |

In one embodiment, the invention provides isolated peptides with an IC$_{50}$ value that is at least lower than the IC$_{50}$ value of WT SALL4 peptide represented by the amino acid sequence MSRRKQAKPQHI (SEQ ID NO: 13). In one embodiment, the invention provides isolated peptides with an IC$_{50}$ value that is at least lower than about 1.0 μM. In a different embodiment, the invention provides peptides with an IC$_{50}$ value that is at least lower than about 0.5 μM. In another embodiment, the invention provides isolated peptides with an IC$_{50}$ value that is at least lower than about 0.25 μM. In yet another embodiment, the invention provides isolated peptides with an IC$_{50}$ value that is at least lower than about 0.1 μM. In another embodiment, the invention provides isolated peptides with an IC$_{50}$ value that is at least lower than about 0.05 μM.

In one embodiment, the invention provides isolated peptides with a K$_D$ value that is at least lower than the K$_D$ value of WT SALL4 peptide represented by the amino acid sequence MSRRKQAKPQHI (SEQ ID NO: 13). In one embodiment, the invention provides isolated peptides with a K$_D$ value that is at least lower than about 1.0 μM. In a different embodiment, the invention provides isolated peptides with a K$_D$ value that is at least lower than about 0.5 μM. In another embodiment, the invention provides isolated peptides with a K$_D$ value that is at least lower than about 0.25 μM. In yet another embodiment, the invention provides isolated peptides with a K$_D$ value that is at least lower than about 0.1 μM. In another embodiment, the invention provides isolated peptides with a K$_D$ value that is at least lower than about 0.05 μM. The term "about" as used throughout this application refers to a value that is +10% of the value the term precedes or denotes.

In one embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13). In another embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding inhibits the activity of RBBp4. In another embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding inhibits the interaction between WT SALL4 peptide of SEQ ID NO: 13 and the RBBp4 protein. In one embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding inhibits the expression of SALL4. In another embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding inhibits the functional activity of SALL4. In another embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding inhibits the downstream signaling of SALL4. In one embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding promotes the expression of Phosphatase and Tensin Homolog (PTEN). In another embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the binding promotes the functional activity of Phosphatase and Tensin Homolog (PTEN). "Inhibiting" as used herein, refers to blocking or preventing. "Promotes" as used herein, refers to increasing or enhancing.

In one embodiment, the invention provides isolated peptides that bind to the same binding site of the histone binding protein RBBp4 with higher binding affinity than the WT SALL4 peptide represented by the amino acid sequence MSRRKQAKPQHI (SEQ ID NO: 13), wherein the isolated peptide is 10 or 11 amino acids long.

As used herein, "SALL4" refers to a zinc finger transcription factor essential in the developmental stage, as it is a potent stem cell factor. SALL4 forms a core transcriptional network with Oct4, Nanog and Sox2, and governs the self-renewal property of murine embryonic stem cells (ESCs). As used herein, "RBBp4" refers to retinoblastoma binding protein 4, a Histone-binding protein that is part of a bigger Mi-2/NuRD complex. This complex has been implicated in chromatin remodeling and transcriptional repression associated with histone deacetylation.

Isolated peptides of the current invention can be used for various applications, for instance as a pharmaceutical formulation for the treatment of hepatocellular carcinoma (see, e.g., the Examples and FIGS. 4-7 of this application). Alternatively, the isolated peptides of the present invention, can be used for the treatment and diagnosis of various other therapeutic applications including, but not limited to, autoimmune diseases, inflammatory diseases, solid tumors, hematological tumors and others.

Accordingly, the present invention also encompasses pharmaceutical compositions comprising at least one of the isolated peptides described in this invention. In some embodiments, the invention provides pharmaceutical compositions comprising at least one of the isolated peptides described in this invention covalently linked to the C or the N-terminal extremity of a cell penetrating peptide. In a particular embodiment, the invention provides pharmaceutical compositions comprising at least one of the isolated peptides described in this invention covalently linked to the C or the N-terminal extremity of the cell penetrating peptide comprising an amino acid sequence set forth in RQIKIWFQNRRMKWKK (SEQ ID NO: 2). In a particular embodiment, the pharmaceutical composition comprises an isolated peptide with the amino acid sequence RRKFAKFQWI (SEQ ID NO: 14).

In certain embodiments, the pharmaceutical compositions of the invention described herein are formulated for therapeutic (e.g., pharmaceutical) use with one or more pharmaceutically-acceptable carriers or excipients. Generally, pharmaceutically-acceptable carriers or excipients may be present in the in amounts having no substantial effect on the stability and release rate profiles the hydrophobic compound (s) in the composition. Suitable excipients/carriers are well known in the art, including those described in Gennaro et al., Remington's Pharmaceutical Sciences (18th ed., Mack Publishing Company, 1990, see especially Part 8: Pharmaceutical Preparations and their Manufacture), which is incorporated herein by reference in its entirety.

The pharmaceutical compositions of the invention can be in a solid form or liquid form. Typically, they are in dosage unit form, such as tablet, powder, sachet, bead, pellet, osmotic dosage form, etc., but they may as well be in a liquid, cream or aerosol form for use in various applications, (for, e.g., topical, parenteral, oral, buccal, ophthalmic, nasal, dermal, rectal, and pulmonary routes).

The pharmaceutical compositions of the present invention can be formulated for different modes of administration, including, but not limited to, parenteral, oral, buccal, ophthalmic, nasal, dermal, rectal, and pulmonary routes. In one embodiment, the compositions are in an oral delivery form, such as a tablet, capsule or osmotic dosage form. In another embodiment, the compositions are in a form suitable for administration by injection. In another embodiment, the compositions are administered intravenously. In one embodiment, the compositions are in a topical delivery form, such as a gel, powder or ointment form. In another embodiment, the compositions are in a form suitable for administration by implantation.

Methods of Inhibition and Treatment

SALL4 has multiple functions. It can activate genes or repress genes. It is known that SALL4 is down-regulated or absent in most adult tissues but is re-activated in many disease states including cancers. It was reported earlier that the interaction of SALL4 with NuRD complex played an important role in promoting tumorigenesis in cells that express SALL4. One of the mechanisms underlying SALL4-induced tumorigenesis is the suppression of tumor suppressor gene PTEN through its interaction with NuRD complex. Thus, the present invention discloses the use specific isolated peptides described herein for the disruption of SALL-NuRD, particularly the interaction of SALL4-RBBp4 protein.

Accordingly, the present invention provides, in various embodiments, methods for inhibiting the binding of a Sal-like protein 4 (SALL4) with histone-binding protein RBBp4 in a cell expressing SALL4. The method comprises contacting the cell with at least one of the isolated peptides described in the text of this application. Binding of at least one of the isolated peptide to RBBP4 disrupts the SALL4-RBBp4 interaction, thereby inhibiting SALL4. In the methods described herein, inhibiting SALL4 can include inhibiting the activity of SALL4, the expression of SALL4 or a combination thereof. That is, any one of the isolated peptides of the current invention can partially or completely down regulate (decrease) SALL4 expression and/or activity. In a particular embodiment, the method comprises contacting a cell expressing high levels of SALL4 with at least one of the isolated peptides described herein. In another embodiment, the method comprises contacting a cell expressing low levels of SALL4 with at least one of the isolated peptides described herein. In yet another embodiment, the method comprises contacting a cell that does not express SALL4 with at least one of the isolated peptides described herein. In any one of the embodiments described above, the "at least one isolated peptide" refers to the isolated peptide with the amino acid sequence RRKFAKFQWI (SEQ ID NO: 14).

The term "cell" as used herein, refers to any living cell. Such living cells may include, but are not limited to, mammalian cells, bacterial cells, or plant cells. Further, a living cell may be derived from a "subject", or a living cell may be derived from cell lines. Cells lines may include, but are not limited to, HEK-293T cells, HT1080 cells, HeLa cells, Daudi cells, K562 cells, or COS cells.

As will be appreciated by those of skill in the art, high levels of SALL4 refer to increased amounts of SALL4, typically found in patients with certain tumors, as compared to the low level of SALL4 in a normal (e.g., healthy) cell (e.g., a non-tumor cell) or in a normal individual (an individual that does not have a tumor). For example, a high level of SALL4 refers to an increased level of SALL4 present in an individual that has a liver tumor (e.g., a tissue and/or cell from an individual's liver tumor) when compared to the level of SALL4 present in an individual that does not have a liver tumor (e.g., a tissue and/or cell from an individual's liver wherein the individual does not have a liver tumor, such as a healthy individual).

In one embodiment, the invention provides a method for inhibiting the binding of SALL4 with histone-binding protein RBBp4 in a cell expressing SALL4, wherein the cell is malignant. The term "malignant" as used herein, refers to any cell or tissue expressing SALL4 that exhibits uncontrolled, excessive growth or proliferation. In another embodiment, the invention provides a method for inhibiting the binding of SALL4 with histone-binding protein RBBp4 in a malignant cell expressing SALL4, wherein the inhibition of binding of SALL4 with RBBp4 reduces the proliferation of the malignant cells. In yet another embodiment, the invention provides a method for inhibiting the binding of SALL4 with histone-binding protein RBBp4 in a malignant cell expressing SALL4, wherein the inhibition of binding of SALL4 with RBBp4 inhibits the proliferation of the malignant cells.

The present invention also provides a method for treating a subject having a disorder mediated by a dysregulation of SALL4. The term "dysregulation" as used herein, refers to altering the expression and/or function of upstream or downstream targets of SALL4. For example, the downstream targets include, but are not limited to RBBp4, PTEN and others. Examples of other targets include, but are not limited to phosphor AKT, CCND2, OCT4, ZNHIT6, WKN1, SNHG12 and others. The method comprises administering a therapeutically effective amount of the pharmaceutical composition described herein to the subject (e.g., a subject in need thereof). A "pharmaceutical composition" comprises an (one or more) isolated peptide described herein as the active ingredient and inert ingredient(s), such as physiologically or pharmaceutically acceptable excipients, that make up the carrier. Apart from the above specified peptides it is also possible to use functionally equivalent homologues or analogues thereof, including those that mimic the three-dimensional structure of the corresponding segment in SALL4 due to the introduction of structural constraints or other chemical constraints. In a particular embodiment, the pharmaceutical composition of the method for treating a subject having a disorder mediated by a dysregulation of SALL4 described herein comprises an isolated peptide with the amino acid sequence RRKFAKFQWI (SEQ ID NO: 14).

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "treat," "treating," or "treatment," mean to counteract a medical condition (e.g., localized inflammation) to the extent that the medical condition is improved according to a clinically-acceptable standard (e.g., reduction or elimination of the localized inflammation). The term "disorder" as used herein, refers to any impairment of the normal state of the living animal or plant body or one of its parts that interrupts or modifies the performance of vital functions that is typically manifested by distinguishing signs and symptoms. For example, a disorder may include, but is not limited to, cancer diseases, cardiovascular diseases, neurodegenerative diseases, immunologic diseases, autoimmune diseases, inherited diseases, infectious diseases, bone diseases, and environmental diseases.

As used herein, "subject" refers to a vertebrate or a mammal (e.g., human, non-human primate, cow, sheep, goat, horse, dog, cat, rabbits, guinea pig, rat and mouse). In a particular embodiment, the subject is a human. In a different embodiment, the subject is a veterinary animal. Examples of veterinary animals include, but not limited to cow, pig, sheep, goat, horse, dog, cat, rabbits, guinea pig and others. A "subject in need thereof" refers to a subject (e.g., patient) who has, or is at risk for developing, a disease or condition that can be treated (e.g., improved, ameliorated, prevented) by at least one of the isolated peptides to be administered.

The pharmaceutical composition of the method for treating a subject having a disorder mediated by a dysregulation of SALL4 described herein can be administered to the subject as a prophylactic or therapeutic composition (e.g., to prevent or treat a disease or condition) or, alternatively, as a diagnostic composition (e.g., a nutraceutical or cosmetic composition). Any suitable route of administration can be used, for example, oral, dietary, topical, transdermal, rectal, parenteral (e.g., intravenous, intraarterial, intramuscular, subcutaneous injection, intradermal injection), inhalation (e.g., intrabronchial, intranasal or oral inhalation, intranasal drops), ocular, pulmonary, nasal, and the like may be employed. Administration can be local or systemic as indicated. The preferred mode of administration can vary depending on the particular agent chosen. Suitable dosage forms include tablets, troches, dispersions, suspensions, solutions, capsules, creams, ointments, aerosols, and the like. The pharmaceutical composition can be administered in a single dose (e.g., in a day) or in multiple doses. In addition, the compound can be administered in one or more days (e.g., over several consecutive days or non-consecutive days).

In certain embodiments of the method for treating a subject having a disorder mediated by a dysregulation of SALL4 described herein, a therapeutically effective amount of a pharmaceutical composition comprising at least one of the isolated peptides described in the current invention is administered to a subject in need thereof. As used herein, "therapeutically effective amount" or "effective amount" means an amount of the active compound (e.g., at least one of the isolated peptides described in the current invention) that will elicit the desired biological or medical response in a tissue, system, subject, or human, which includes alleviation of the symptoms, in whole or in part, of the condition (for, e.g., tumor) being treated. In certain embodiments, pharmaceutical compositions described in this invention, when administered to a subject, is sufficient to achieve a desired therapeutic effect in the subject under the conditions of administration, such as an amount sufficient to inhibit (e.g., prevent, reduce, eliminate) an upstream or downstream target of SALL4 (e.g., PTEN) in the subject.

In certain embodiments, the present invention also discloses a method for treating a subject having a cancer by administering to a subject in need thereof, pharmaceutical compositions comprising isolated peptides described in the present invention. In certain embodiments, pharmaceutical compositions described in the method herein are administered to subject having cancer expressing SALL4. In certain other embodiments, pharmaceutical compositions described in the method herein are administered to subject having solid tumors expressing SALL4. In other embodiments, pharmaceutical compositions described in the method herein are administered to subject having subtypes of solid tumors expressing SALL4, including some clinically challenging cancers. In some embodiments, the solid tumor expresses high levels of SALL4. In one embodiment, the solid tumor has reduced expression of PTEN. In some embodiments, administering the pharmaceutical compositions comprising isolated peptides described in the present invention inhibits the activity or expression of SALL4. In other embodiments administering the pharmaceutical compositions comprising isolated peptides described in the present invention inhibits the activity and expression of SALL4. In a particular embodiment of the method, the isolated peptide in the pharmaceutical composition of a method for treating a subject having a cancer is RRKFAKFQWI (SEQ ID NO: 14).

As will be appreciated by those of skill in the art, a solid tumor that can be treated using the methods described herein include a breast tumor, a lung tumor, an ovarian tumor, a liver tumor (e.g., hepatocellular carcinoma), a gastric tumor, a brain tumor, a germ cell tumor etc. In one aspect, the solid tumor is a liver tumor. In another aspect, the solid tumor is a lung tumor (e.g., NSCLC). In a particular aspect, the lung tumor comprises cells that are epidermal growth factor receptor (EGFR)-mutation positive, EGFR-mutation negative or a combination thereof. In another aspect, the solid tumor is a brain tumor. In a particular aspect, the brain tumor is a glioblastoma multiforme brain tumor. In yet another aspect, the solid tumor is not a tumor of stem cell or progenitor cell origin.

In one aspect, the invention is directed to a method of treating a (one or more) solid tumor which expresses SALL4 and NuRD in subject in need thereof, comprising administering to the individual an effective amount of a (one or more) composition that inhibits the binding of SALL4 with RBBp4. In another aspect, the invention is directed to a method of treating a liver tumor which expresses SALL4 in an individual in need thereof comprising administering to the individual an effective amount of a composition that inhibits SALL4. In yet another aspect, the invention is directed to a method of treating a (one or more) solid tumor which expresses high levels of SALL4 and low levels of PTEN in subject in need thereof, comprising administering to the subject an effective amount of a (one or more) composition that inhibits the binding of SALL4 with RBBp4 and promotes expression of PTEN. In another aspect, the invention is directed to a method of treating a (one or more) solid tumor which expresses high levels of SALL4 and low levels of PTEN in subject in need thereof, comprising administering to the individual an effective amount of a (one or more) composition that inhibits the binding of SALL4 with RBBp4. and promotes the activity of PTEN.

In certain embodiments, pharmaceutical compositions described in the method herein are administered to subject having cancer, wherein the cancer is a hematological cancer. Examples of hematological cancers include, but are not limited to leukemia (e.g., acute myelogenous leukemia (AML)), lymphoma (e.g., non-Hodgkin lymphoma (NHL) and multiple myeloma. In a particular embodiment of the method, the hematological cancer has cancer cells expressing SALL4.

The terms "comprises", "comprising", "includes", "including", "having" and their conjugates mean "including but not limited to". The term "consisting of" means "including and limited to". As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Exemplification

SALL4 Binds to RBBp4 of NuRD

It was previously reported that SALL4 WT binds to the NURD complex and blocks the SALL4-NuRD interaction. The histone binding protein, RBBp4 was hypothesized to be the subunit in NuRD to which SALL4 binds. To confirm direct binding between SALL4 and RBBp4, a binding assay was performed using the 12 amino acid WT SALL4 T (FIG. 1). Using isothermal titration calorimetry, the direct interaction between SALL4 and the RBBp4 subunit of NURD complex, was demonstrated. The 12-aa SALL4 peptide binds to RBBp4 with a $K_D$ of 1.04±0.06 µM (FIG. 1A). The binding kinetics were further confirmed using surface plasmon resonance, with a calculated $K_D$ for binding between the SALL4 peptide and RBBp4 of 1.5 µM (kon=16830±460 M−1 s−1; koff=0.026±0.00045 s−1) (FIG. 1B). These results demonstrated direct binding of SALL4 to the NuRD complex via its subunit, RBBp4.

Crystal Structure of the RBBp4-SALL4 Complex

Figures 2A, 2B, 2C:
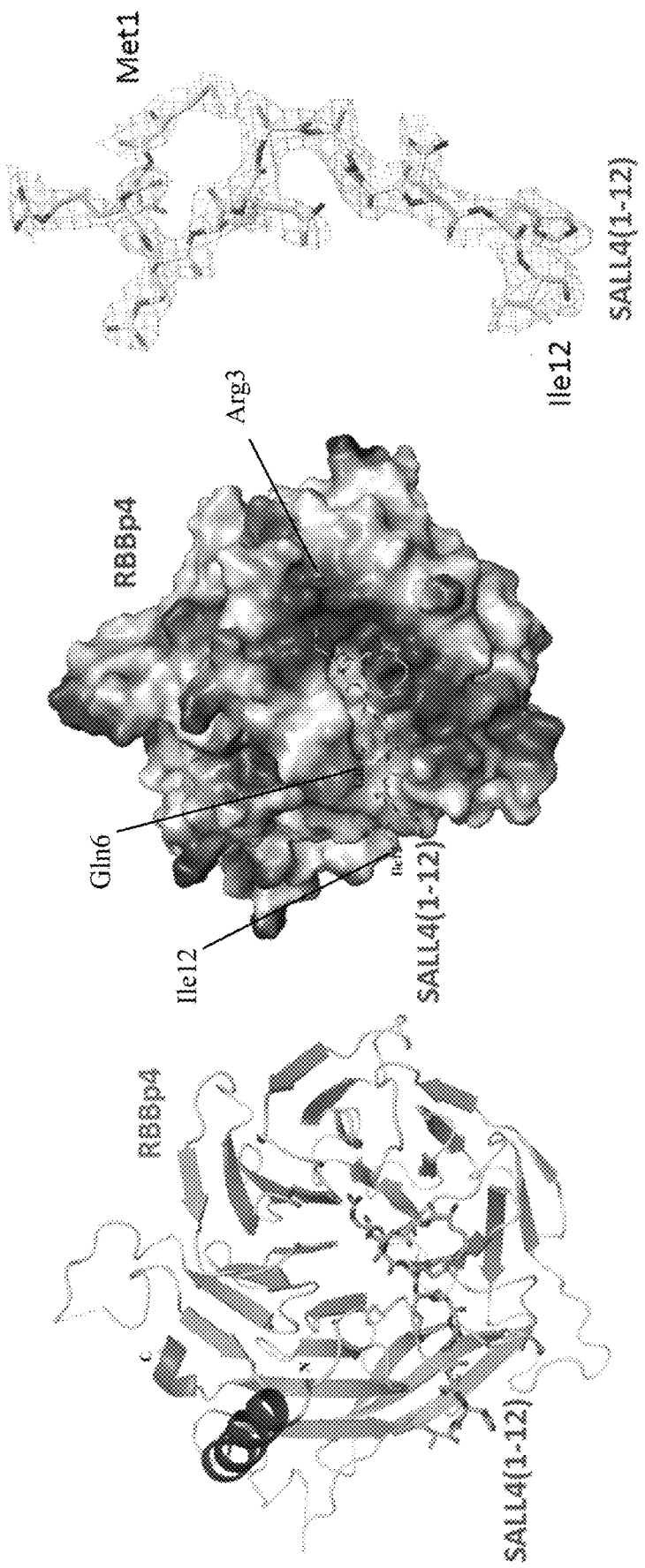
FIGS. 2A-2D. Crystal Structure of SALL4-RBBp4 complex.
Figure 2D:
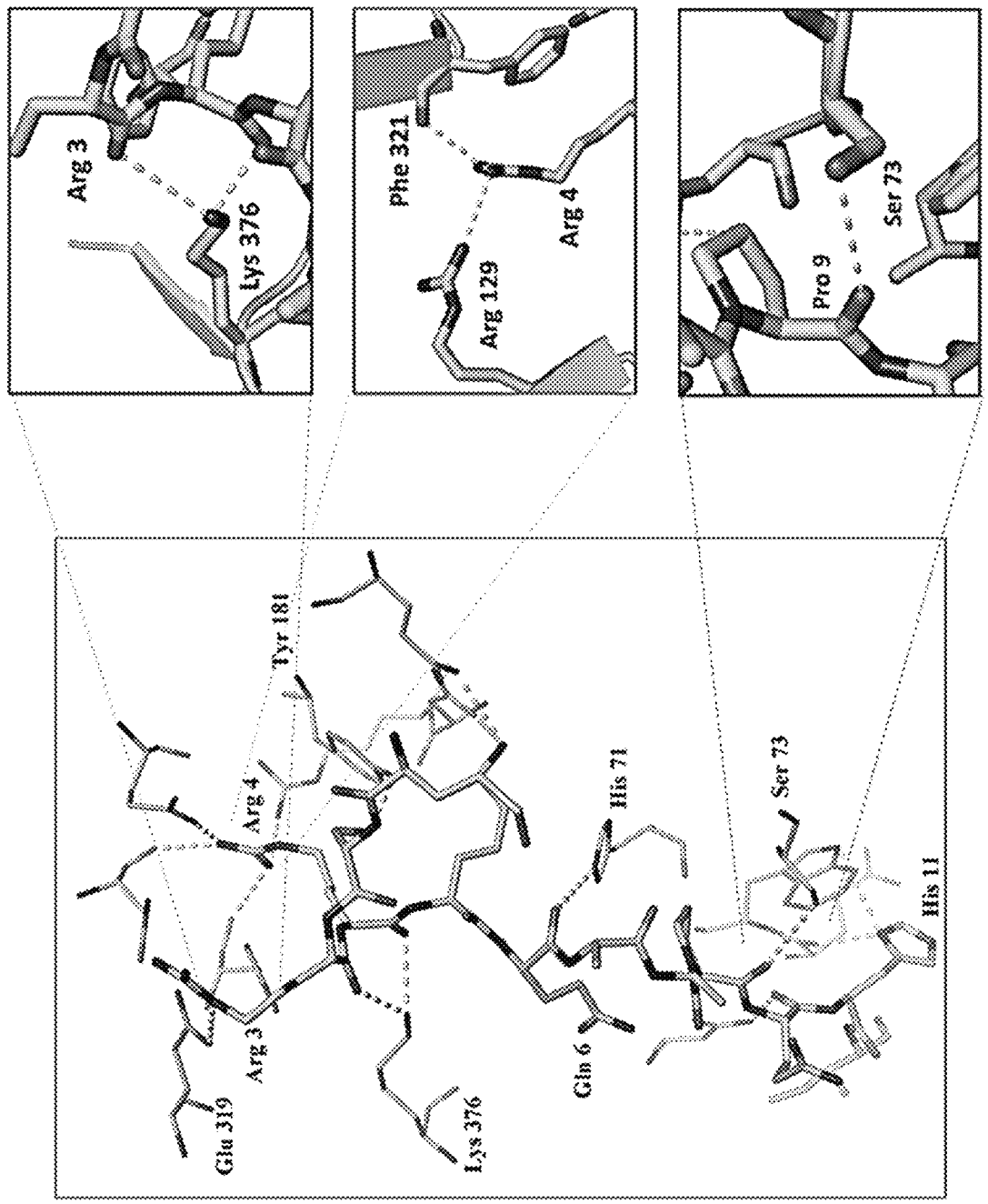

The crystal structure of RBBp4-SALL4 complex was determined to identify the key interactions between the two proteins. The crystal structure of the RBBp4-SALL4 complex was determined at 2.7 Å resolution (FIG. 2). RBBp4 forms a 7-sheet β-propeller (residue 33-404) with an N-terminal α-helix (FIG. 2A). All 12 residues of the SALL4 peptide are well defined in the electron density map, with nine of those residues making favourable interactions with RBBp4. The substrate binding site of RBBp4 is highly acidic, with eight glutamic acid and two aspartic acid residues within 5 Å of the SALL4 peptide. This negatively charged interface binds the predominantly positively charged SALL4 peptide, which has five basic residues: Arg3, Arg4, Lys5, Lys8 and His11 (FIGS. 2B & 2C). Arg3 and Lys5 of SALL4 form charged interactions with Glu275, Glu319 and with Glu126, Glu179, respectively, in RBBp4 (FIG. 2D). The key interactions between SALL4 residues and the residues lining the acidic pocket in RBBP4 are summarized below in Table 2. Residues involved exclusively in SALL4-RBBp4 complex are in bold in Table 2. Arg4 forms a salt bridge with Glu231, whereas His11 makes π-cation interactions with Trp42. Additional hydrogen bonds between residues Ser2 to Gln6 and Gln10 to Ile12 stabilize the SALL4 peptide, and several hydrophobic interactions stabilize the complex (Table 2). The Arg4 side-chain is deeply buried into RBBp4 (buried surface area 211 Å$^2$), whereas Lys5 and Pro9 bind in shallow groves. Several unique hydrogen bonding contacts are observed in the SALL4-RBBp4 complex (FIG. 2C, Table 2). Further, it was observed that the non-conserved Gln10 and His11 of SALL4 form a hydrogen bond with Asn397 and Glu41, Trp42 of RBBp4, respectively.

TABLE 2

| RBBp4 (atom) | SALL4 peptide (atom) | Distance (Å) (<3.5 Å) |
|---|---|---|
| 181 Tyr (OH) | 2 Ser (OG) | 3.42 |
| 275 Glu (OE2) | 3 Arg (NH2) | 3.33 |
| 319 Glu (OE2) | 3 Arg (NH1) | 3.45 |
| 376 Lys (NZ) | 3 Arg (O) | 3.39 |
| 277 Asn (O) | 4 Arg (NH1) | 3.07 |
| 231 Glu (OE1) | 4 Arg (NH1) | 2.83 |

TABLE 2-continued

| RBBp4 (atom) | SALL4 peptide (atom) | Distance (Å) (<3.5 Å) |
|---|---|---|
| 321 Phe (O) | 4 Arg (NH2) | 3.43 |
| 129 Arg (NH2) | 4 Arg (NH2) | 3.37 |
| 376 Lys (NZ) | 4 Arg (O) | 2.80 |
| 128 Asn (OD1) | 5 Lys (NZ) | 3.38 |
| 179 Glu (OE1) | 5 Lys (NZ) | 3.25 |
| 181 Tyr (OH) | 5 Lys (NZ) | 3.50 |
| 126 Glu (OE2) | 5 Lys (NZ) | 2.95 |
| 179 Glu (OE1) | 5 Lys (NZ) | 2.50 |
| 395 Glu (OE1) | 6 Gln (OE1) | 3.45 |
| 395 Glu (OE2) | 6 Gln (OE1) | 3.44 |
| 395 Glu (O) | 6 Gln (OE1) | 3.50 |
| 71 His (NE2) | 6 Gln (O) | 3.50 |
| 73 Ser (OG) | 9 Pro (O) | 3.44 |
| 397 Asn (ND2) | 10 Gln (O) | 3.05 |
| 41 Glu (O) | 11 His (ND1) | 3.44 |
| 42 Trp (NE1) | 11 His (ND1) | 3.47 |
| 41 Glu (O) | 12 Ile (N) | 3.39 |

Figures 3A, 3B:
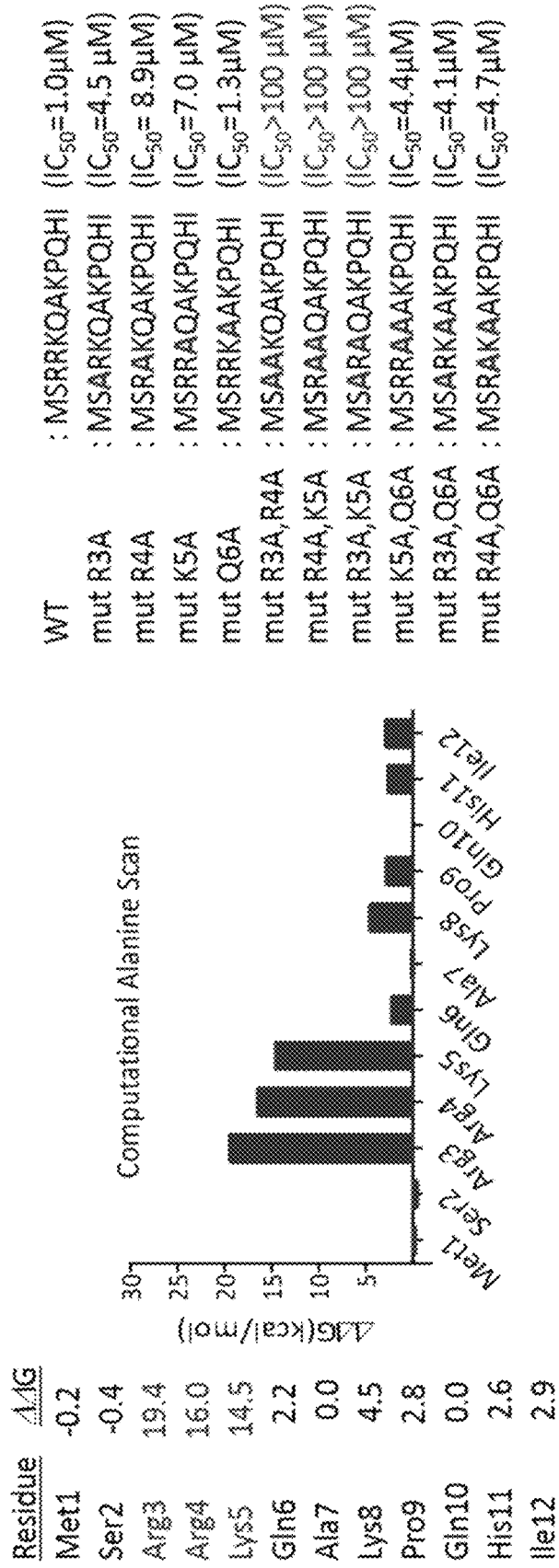
FIGS. 3A-3E. Key residues involved in SALL4 (1-12)-RBBp4 binding.
Figure 3C:
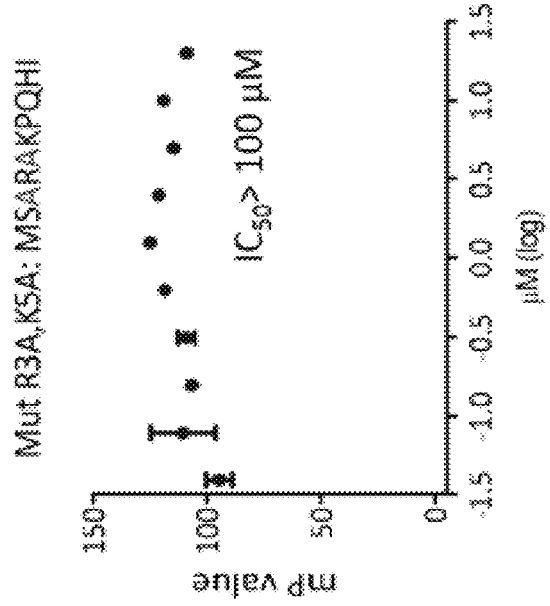
Figure 8:
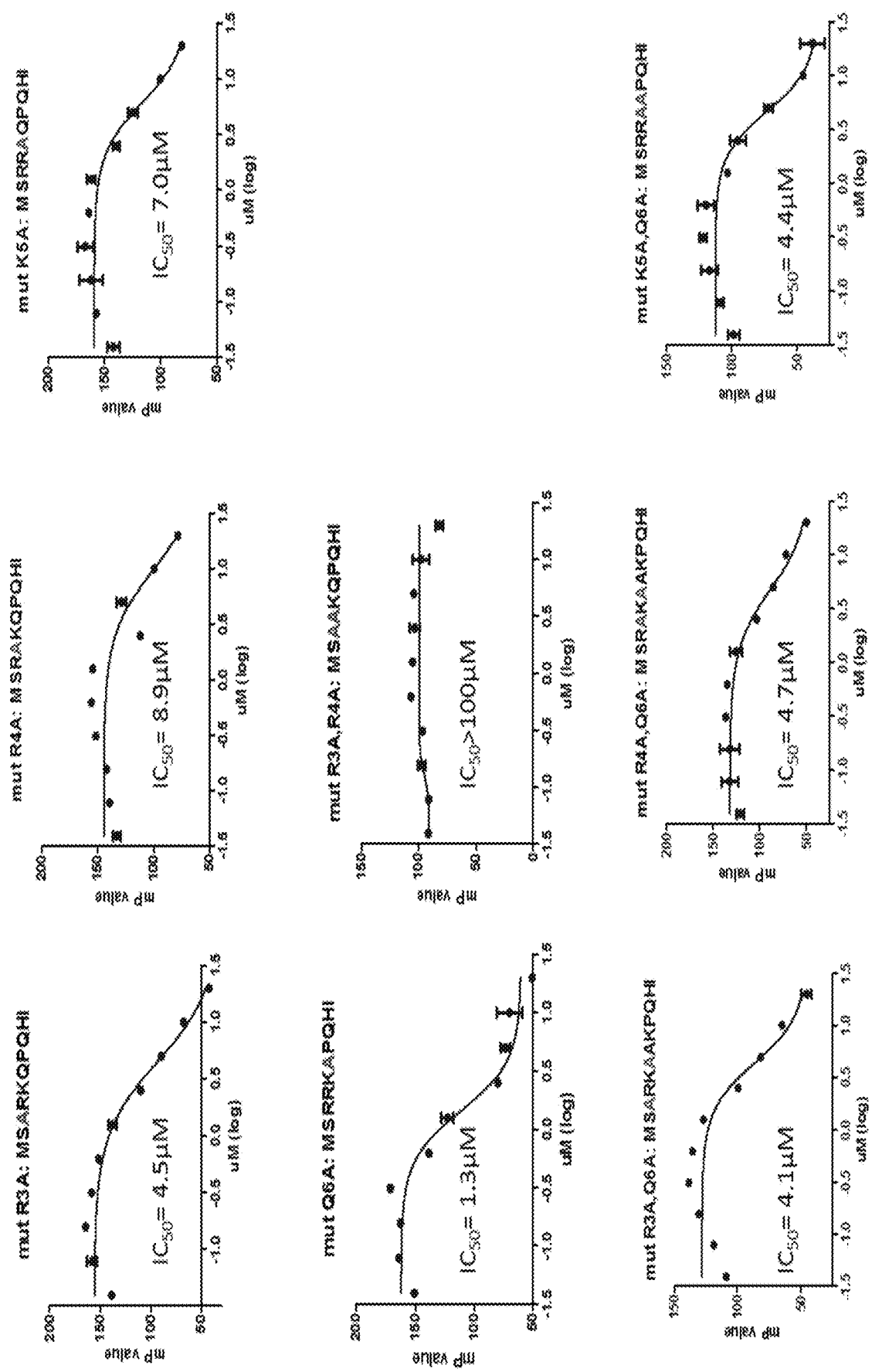
FIG. 8. Representative $IC_{50}$ curves of SALL4 mutant peptides was determined by Fluorescence Polarization (FP).

Computational Analysis Identifies RRK Residues as Essential for RBBp4SALL4 Interaction Structural analysis of the RBBp4-SALL4 complex indicated that Arg3, Arg4 and Lys5 of SALL4 were essential for binding. In silico analysis using computational alanine scanning was performed on the key residues identified by the crystal contacts. Alanine substitutions of Arg3, Arg4 and Lys5 greatly affected the binding free energy (19, 16, and 14 kcal/mol, respectively) (FIG. 3A). A biochemical alanine scan of the residues that affected the binding free energy was performed with a series of mutant peptides using a fluorescence polarization assay (FIG. 3B, 3C and FIG. 8). Compared to the WT SALL4 peptide (IC50=1.0 µM), peptides bearing R3A, R4A or K5A mutations demonstrated significantly decreased $IC_{50}$ values (3.8 µM, 8.9 µM and 7 µM, respectively, FIG. 3B), whereas the Q6A mutation had a minimal effect (IC50=1.3 µM). Double mutations with two key residues—R3A-R4A, R4A-K5A, and R3A-K5A-abolished the interaction, with $IC_{50}$ values noted above 100 µM, whereas double mutants with the loss of only one key residue showed reduced but positive binding (IC50=4.4 µM, 4.1 µM, and 4.7 µM respectively, (FIG. 3B and FIG. 8). These findings confirmed that Arg3, Arg4 and Lys5 are essential residues involved in SALL4-RBBp4 interaction.

Figure 3D:
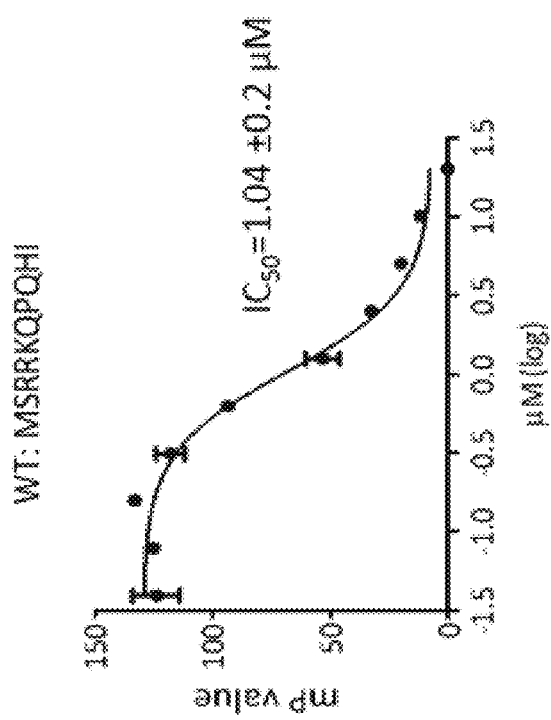
Figure 3E:
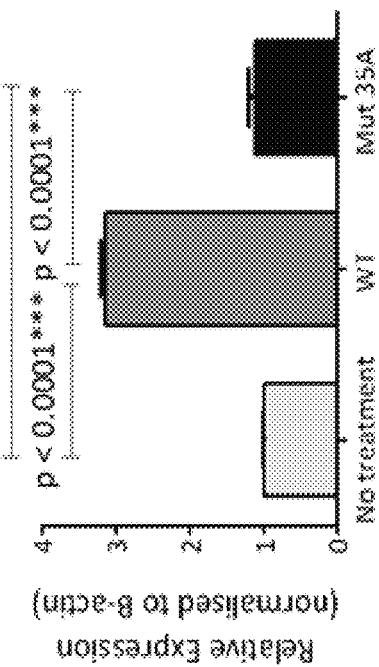
Figure 3E:
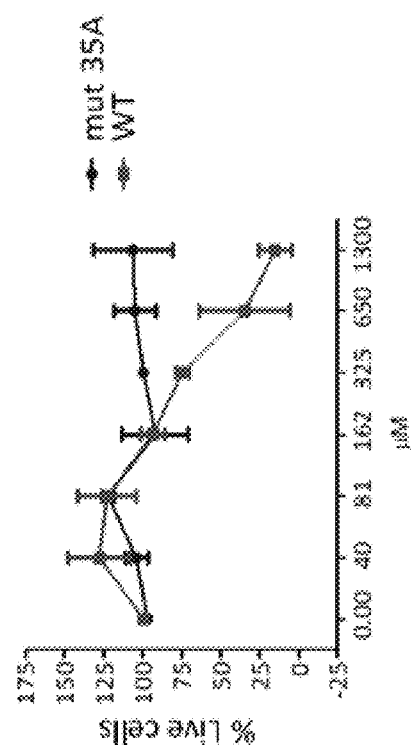

A cell viability assay was performed with a peptide with the sequence MSARAQAKPQHI (labelled as MUT, SEQ ID NO: 39). This peptide had double mutation of two essential residues mutated to alanine, R3A-K5A. Its effect on cell viability was compared with the WT SALL4 peptide on SNU398 HCC cells, which express a high level of SALL4. While the WT peptide exerts an inhibitory effect on cell number, the MUT peptide does not (FIG. 3D). Further Q-PCR analysis revealed a 3-fold increase in PTEN expression (p<0.0001) in cells treated with the WT SALL4 peptide compared to untreated cells, whereas MUT-treated cells again showed no significant change (p-value not significant) (FIG. 3E). These findings indicate that the MUT peptide did not block the RBBp4-SALL4 interaction and therefore failed to release the suppressive complex from the PTEN promoter, unlike its WT counterpart.

Optimization of a Candidate Therapeutic Peptide

Based on the structural data of RBBp4-SALL4 complex, a peptide substrate-based assay was performed to select and optimize peptide inhibitors of the RBBp4-SALL4 interaction. The minimum length of the peptide required for bioactivity was determined through a truncation analysis of the WT peptide (Table 1; peptides 2-7). Removing the first two N-terminal residues, Met and Ser (peptide 5 and 6; Table 1), increased the peptide binding affinity to RBBp4 as compared with the WT ($IC_{50}$=0.60 and 0.36 vs. 1.30 µM, respectively); yet, C-terminal truncations resulted in a marginal loss of binding affinity ($IC_{50}$=1.40, 0.80, and 1.96 µM for peptides 2, 3, and 4, respectively). To further improve binding potency, peptide 6 was selected as the sequence template and subjected to a systematic single-residue mutation analysis with alanine substitutions. Substituting the non-essential residues of peptide 6 with Ala (Table 1; peptides 11 to 16 respectively) yielded more potent peptides. This suggests that they could be replaced with other amino acid residues for sequence optimization. Results show reduction of IC50 upon replacement of Gln 4, Pro 7, and His 9 of peptide 6. Gln4 sits in a small binding pocket formed by Pro43, His71, and Glu395 of RBBp4, which is able to accommodate amino acid residues with hydrophobic sidechains. Consequently, substituting Gln4 with Leu or Phe (peptides 23 and 24) led to improved binding affinities, particularly Phe, which induced a 7-fold enhancement in binding affinity over that of peptide 6 ($IC_{50}$ 0.05 vs. 0.36 µM; Table 1). Additionally, a Phe substitution (peptide 34) for Pro7 further increased the potency of the peptide ($IC_{50}$ 0.17 vs. 0.36 µM; Table S3). Finally, Trp substitution of His9 improved the binding affinity by 3-fold as compared with that of peptide 6 (IC50 0.12 vs. 0.36 µM; Table 1).

Figure 4A:
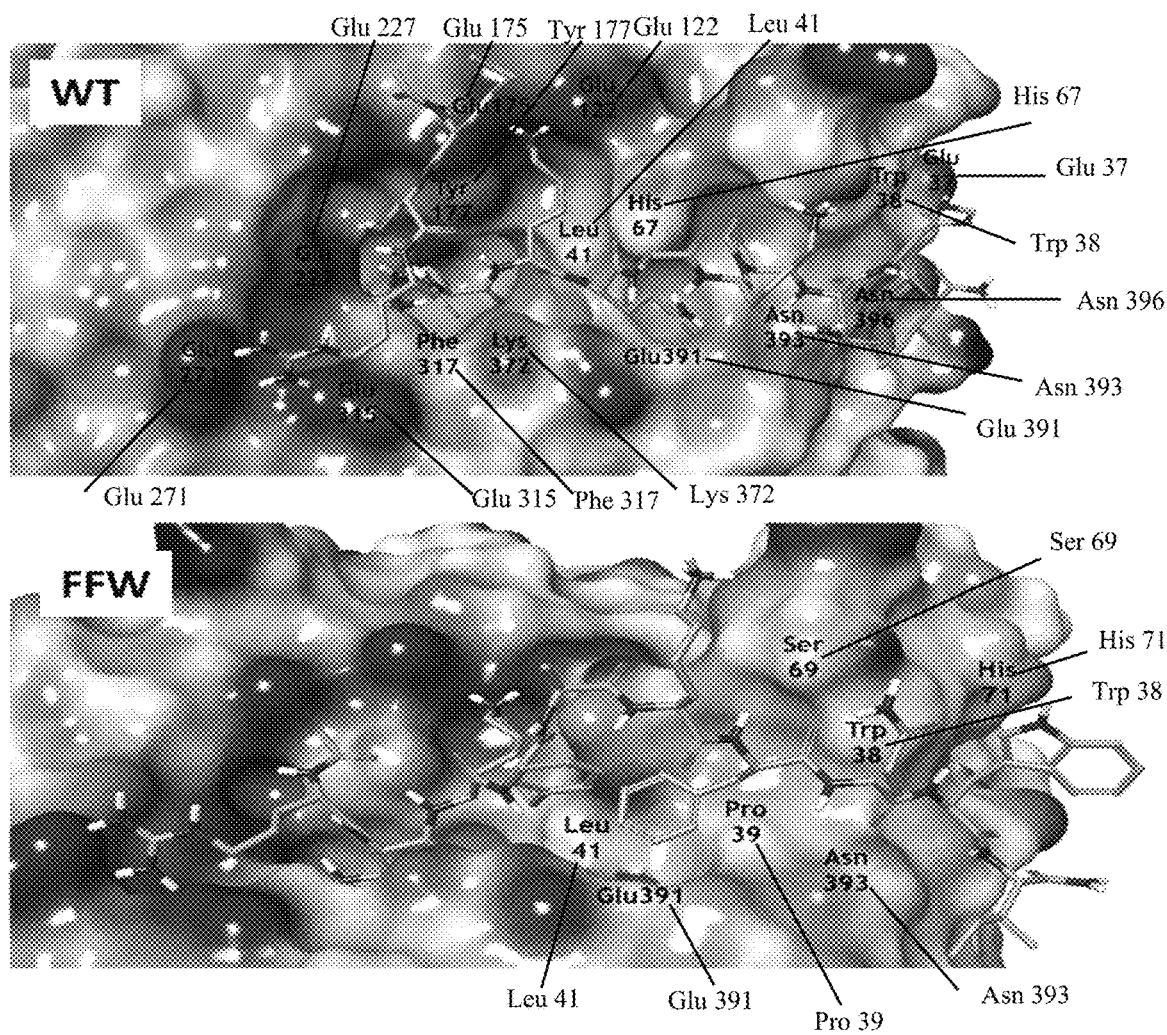
FIGS. 4A-4B. Binding affinity of FFW peptide.
Figure 4B:
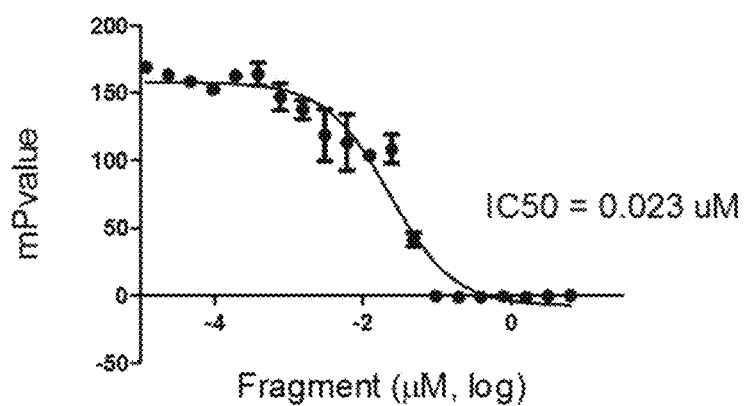

These three substitutions (Gln4Phe, Pro7Phe, and His9Trp) were incorporated into peptide 46 (RRKFAK-FQWI, named FFW hereof, (SEQ ID NO: 14)). Computational modelling of FFW to RBBp4 predicted improvement of binding affinity (FIG. 4A). Fluorescence polarization assay confirmed the high potency of FFW, with a >56-fold increase in affinity as compared with the original 12-residue WT peptide ($IC_{50}$=0.023 vs. 1.30 µM; Table 1, FIG. 4B).

Figures 5A, 5B:
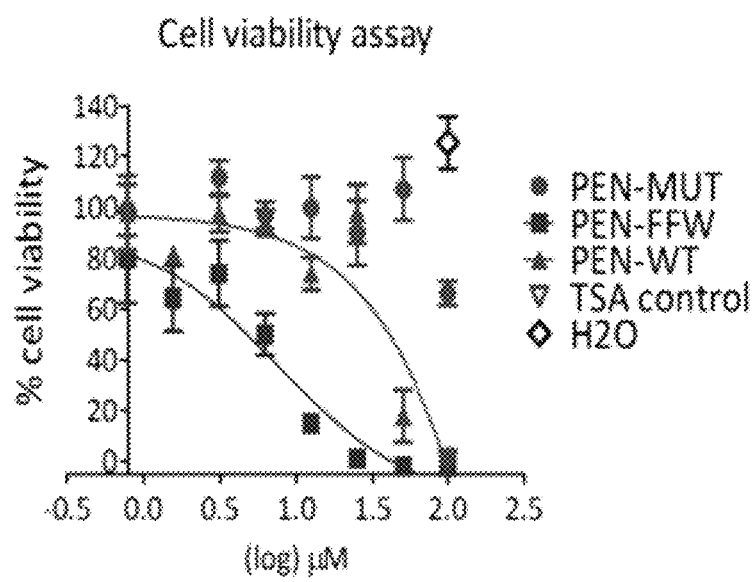
FIGS. 5A-5B. Development of a potent therapeutic peptide FFW.
Figure 6A:
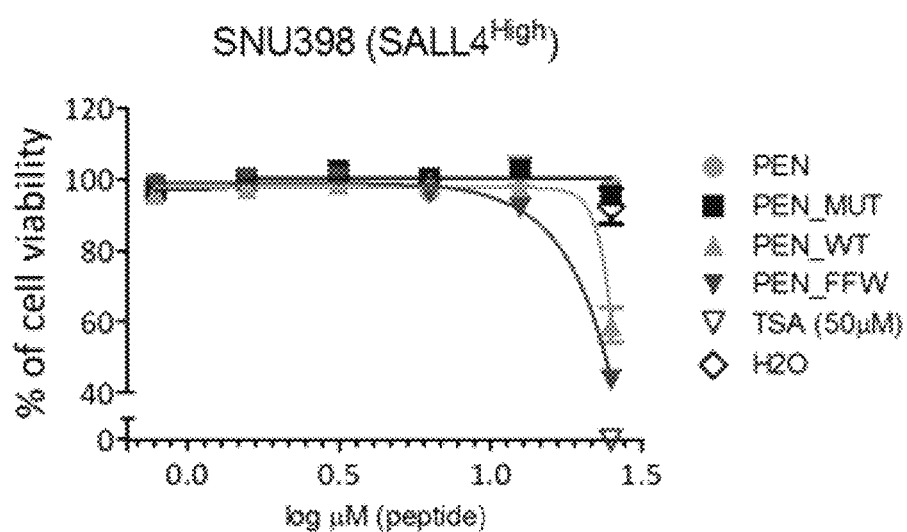
FIGS. 6A-6B. Therapeutic window of PEN-FFW in HCC cell lines.
Figure 6B:
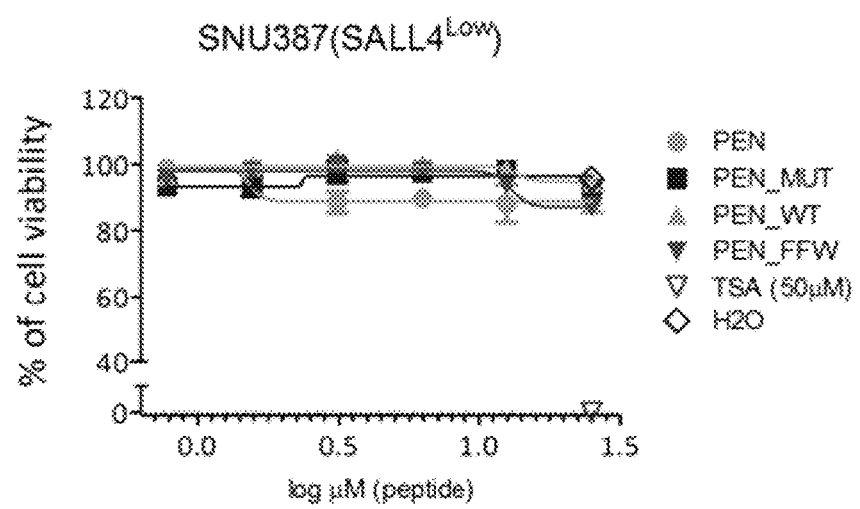

Therapeutic Peptide FFW Inhibits SALL4+ Tumor Cell Growth in Culture and In Vivo The efficacies of the FFW, WT and MUT peptides were compared at the cellular level and in mice. A penetratin sequence (PEN) was attached to the N-terminus of each peptide to facilitate cell penetration in vitro. As shown in FIGS. 5A&B, PEN-FFW conferred a 4-fold improvement in SNU398 cell viability as compared with the PEN-WT (EC50 7.6 µM vs 30 µM), with the PEN-MUT having no significant effect on cell viability (EC50>100 µM). The therapeutic window of PEN-FFW in SALL4 expressing HCC cells was accessed in SNU387 cells, a HCC line with undetectable level of SALL4, as well as SNU398. The MUT and WT SALL4 peptides were also included in this assay for comparison (FIGS. 6 A & B). The results demonstrated the specificity of PEN-FFW in targeting SALL4-high HCC cells (SNU398), highlighting a valuable therapeutic window for treatment.

Figure 7B:
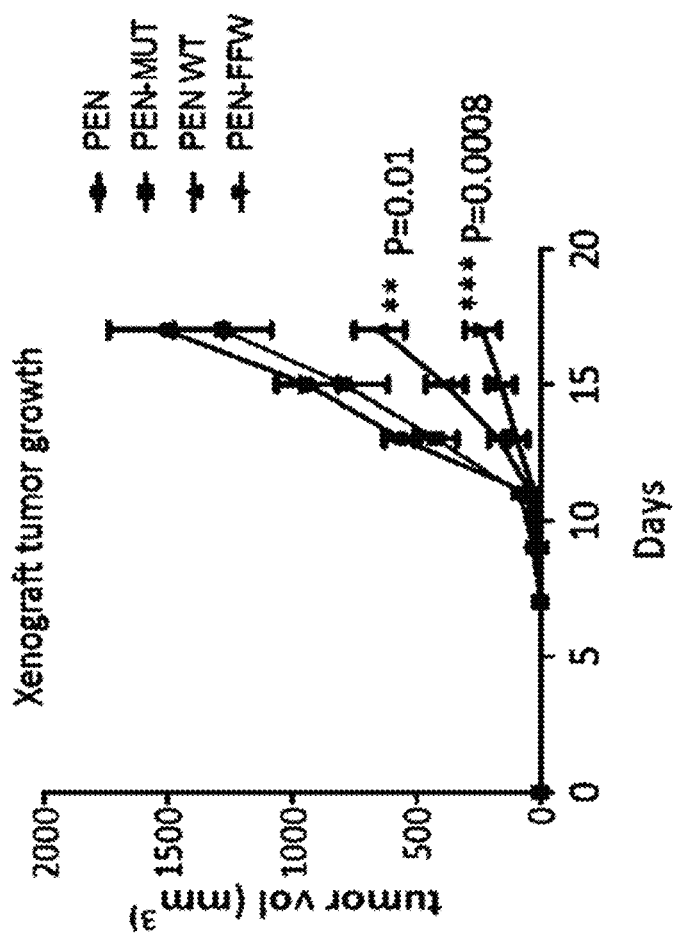
FIGS. 7A-7E. Anti-tumor activity of the candidate therapeutic peptide FFW.
Figure 7A:
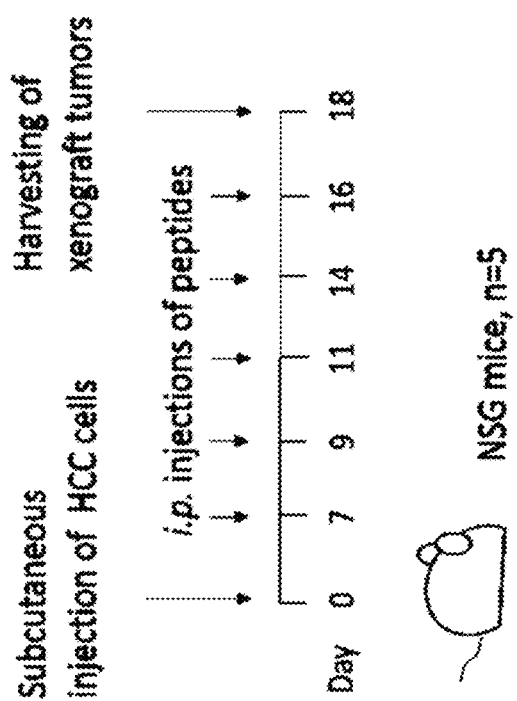
Figure 7D:
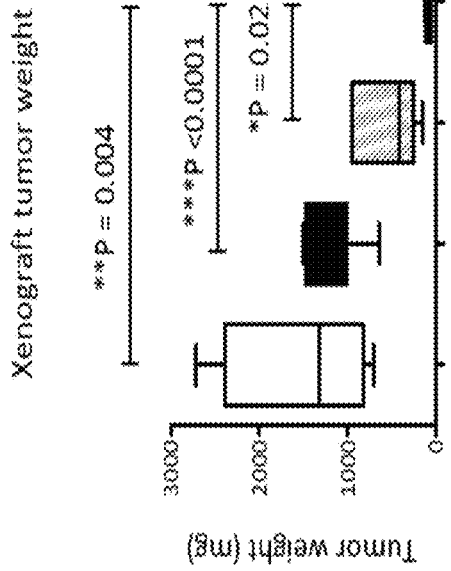
Figure 7C:
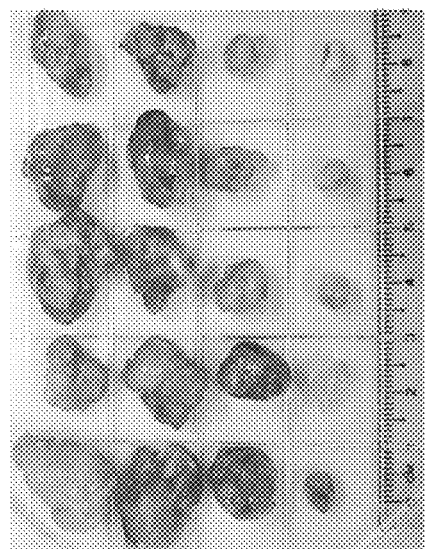
Figure 7E:
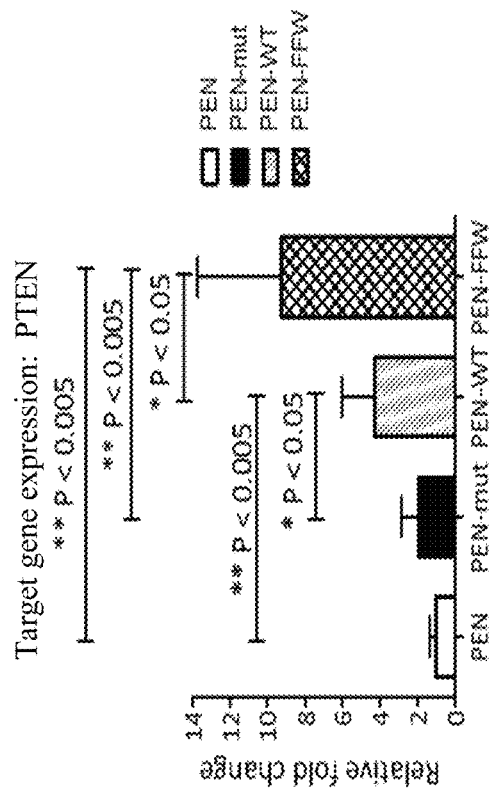

Therapeutic effect of PEN-FFW was studied in vivo. SNU398 cells were implanted subcutaneously into the flanks of NOD/SCID/Gamma mice (NSG) and the mice were randomly grouped for peptide treatments (n=5) (FIG. 7A). For mice treated with PEN (control) or PEN-MUT, tumors progressively increased in size, showing that neither peptide was able to inhibit tumor growth (FIG. 7B). In contrast, although PEN-WT markedly impaired tumor growth (p=0.001), PEN-FFW induced a stronger therapeutic effect (p=0.0008) with a tumor growth inhibition of 85%. PEN-FFW treated mice also displayed the smallest tumors (FIG. 7C), with significantly lower tumor weight (i=88 mg vs. 564 mg in WT, p=0.02; (FIG. 7D). Finally, PTEN mRNA levels in the harvested tumors were measured. A 9-fold increase in PTEN expression was found in tumors from PEN-FFW-treated mice compared to PEN control mice.

Figure 9A:
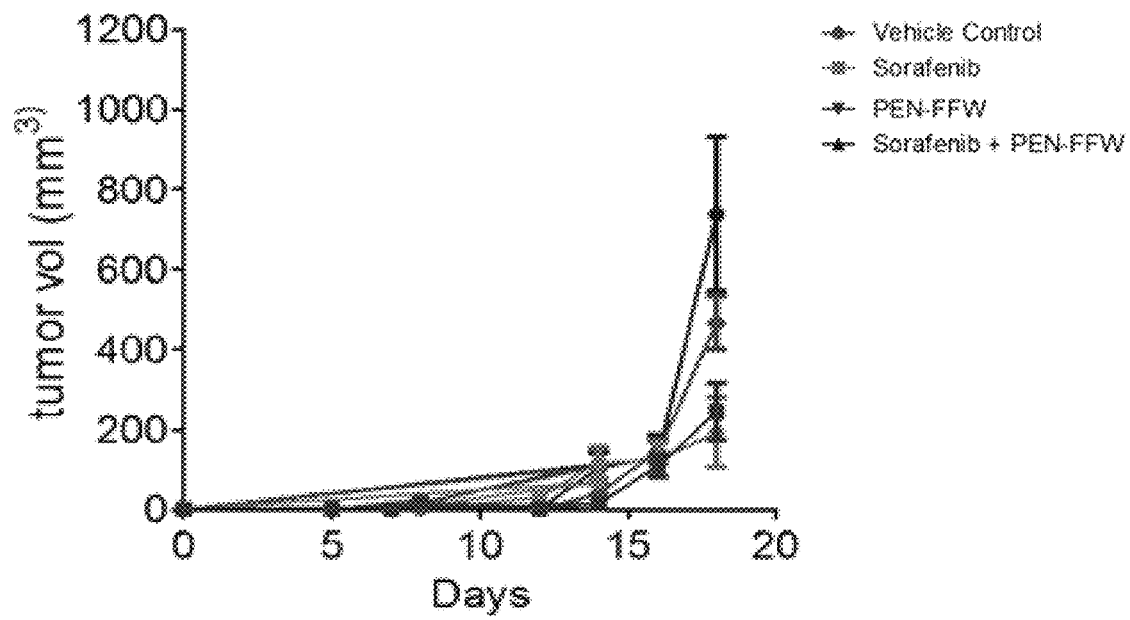
Figure 9B:
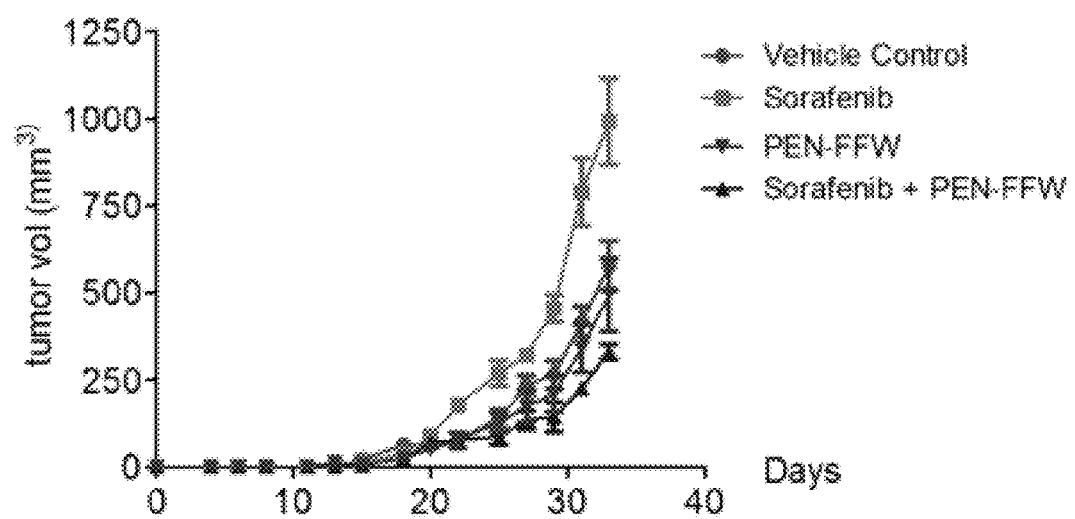

Clinical significance of PEN-FFW was studied in vivo by benchmarking against current therapy using Sorafenib. PEN-FFW treated SNU398 tumor xenografts were compared to that of Sorafenib treated xenografts (FIG. 9A). As shown in FIG. 9A, PEN-FFW treatment resulted in a stronger anti-tumor activity than Sorafenib when compared to vehicle treated groups. Furthermore, mice treated with PEN-FFW in combination with Sorafenib showed the slowest rate of tumor growth. No significant change in mice body weight between the different treatment groups were observed as shown in FIGS. 9C-9E. The results demonstrated—a therapeutic effect of PEN-FFW. Potential therapeutic effect of PEN-FFW in HCC patients that are refractory to Sorafenib treatment was studied also studied in vivo. using a HCC cell line, PLC8024 which is SALL4 positive, CD133+ and is both chemo- and radio-resistant (Li et al., BMC Cancer 2016, 16, 15; Ma et al., Oncogene 2008, 27: 1749-1758), for the xenograft study. As shown in FIG. 9B, a greater tumor growth (+1.5 fold) was observed in the Sorafenib treated group as compared to the control group. PEN-FFW treatment also showed minimal tumor inhibitory effect. However, a synergistic effect of Sorafenib and PEN-FFW was observed (FIG. 9B) in mice treated with both agents (tumor growth inhibition 57% and 73% as compared to control and sorafenib treated group respectively). The results demonstrated the potential use of PEN-FFW in Sorafenib-resistant HCC patients, either alone or in combination with Sorafenib.

Drug Like Property of PEN-FFW with Prolonged Stability and Non-Toxicity

Figure 10A:
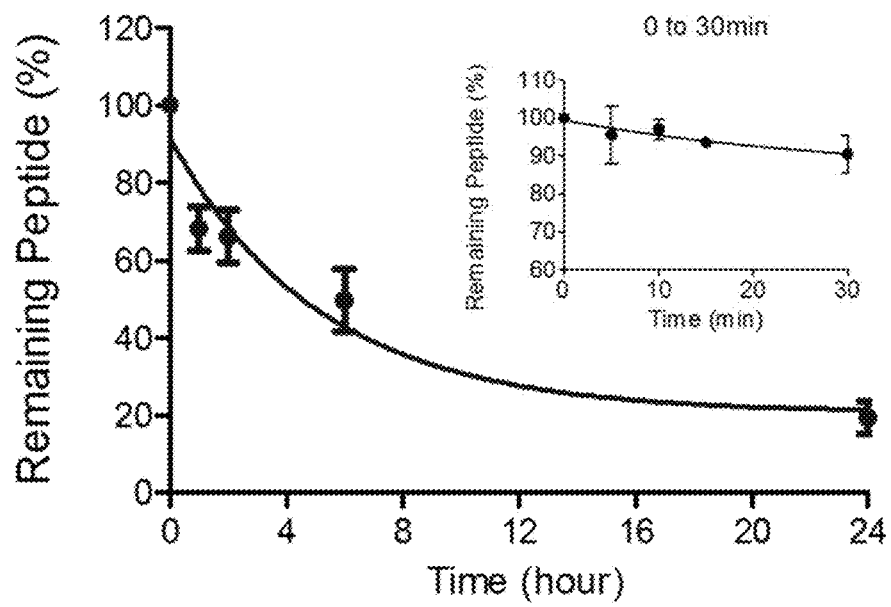
FIGS. 10A-10C. In vitro pharmacokinetics of PEN-FFW in human plasma.
Figure 10B:
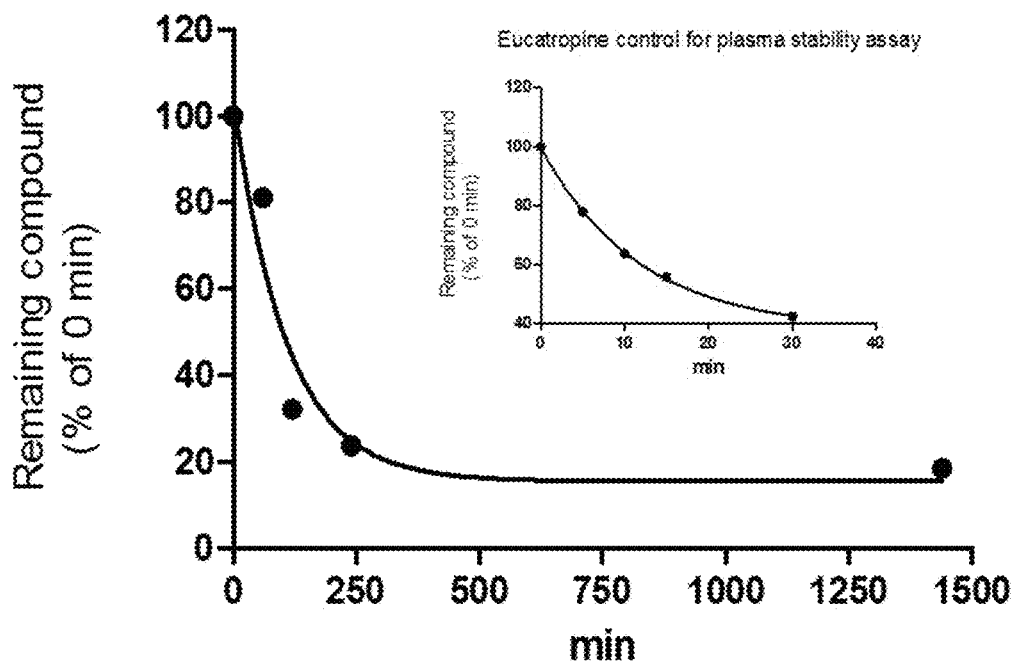
Figure 10C:
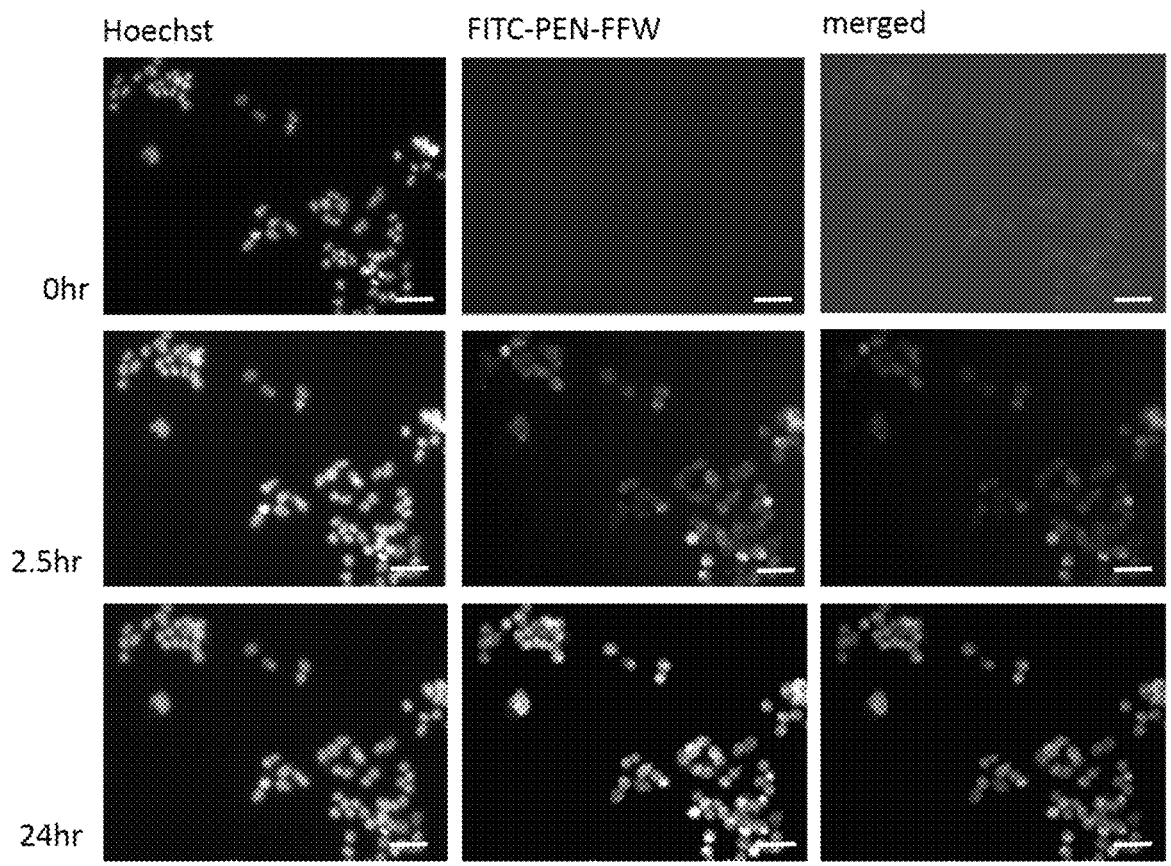

The in vitro pharmacokinetics of PEN-FFW in human plasma was studied by monitoring the degradation of PEN-FFW by LC-MS/MS at after 0, 5, 10, 15 and 30 min incubation (FIG. 10A). PEN-FFW was found to be stable to plasma proteases with more than 90% of the peptide remaining in the plasma after 30 min. In comparison, Eucatropine as the control was rapidly degraded to 40% within 30 min (FIG. 10B). Extending the experiment duration by 24 hour showed more than 50% of the peptide remained intact in the plasma after 4 h, decreasing to ~20% on the 24th hour (FIG. 10A). Results suggest that PEN-FFW is stable and resistant to degradation of plasma proteases and can potentially be developed as an intravenous drug. A FITC tag was conjugated to the N-terminal of PEN-FFW and treated it to the SNU398 cells. Live cell imaging was performed on these cells at 2 min interval for the first one hour, and at 5 min interval for the subsequent 23 hr to assess the permeability and stability of FITC-PEN-FFW. As shown in FIG. 10C, FITC-PEN-FFW started penetrating cells at t=18 min, and completed the nucleus localization at t=22 min. All cells were penetrated by FITC-PEN-FFW at 2.5 hr with gradual increment of its expression up to 24 hr (FIG. 10C, middle and lower panels respectively).

Figures 11C, 11D:
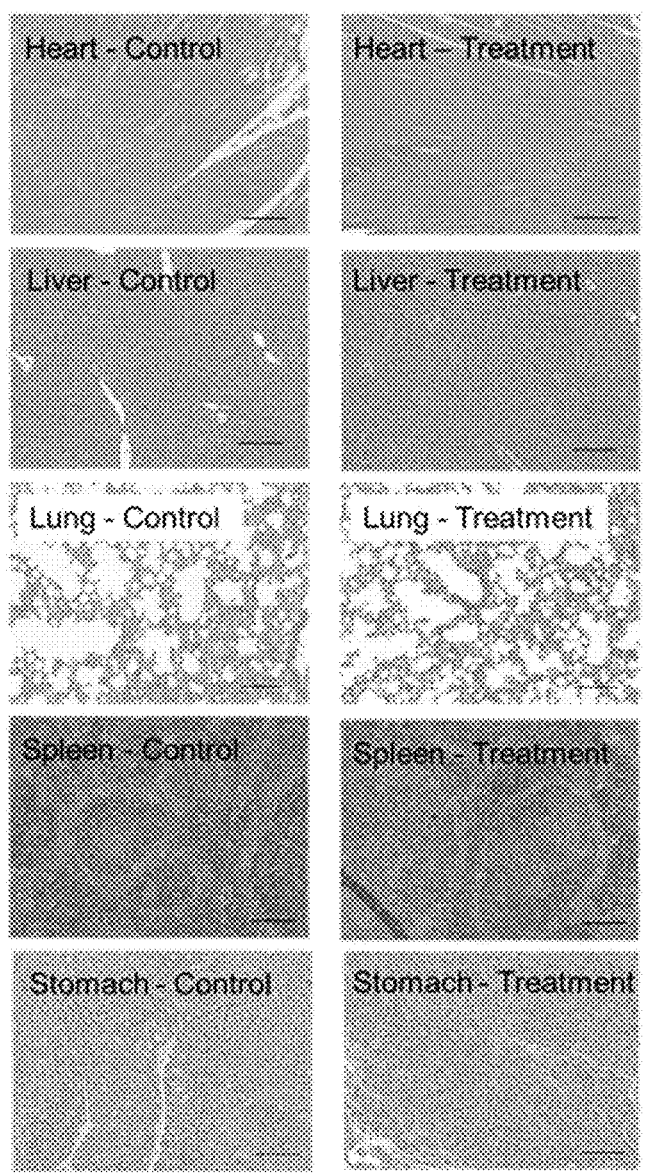

Toxicity of PEN-FFW was studied in vivo in C57BL/6 mice (n=4). Theses mice were exposed to intraperitoneal (IP) administration of PEN-FFW (30 mg/kg) or vehicle (10% DMSO) every alternate day over the course of 17 days to a cumulative dose of 270 mg/kg. Mice in both groups remained alert, responsive and did not exhibit notable signs of toxicity such as weight loss, lethargy or loss of mobility. (FIG. 11A). After a 7-day washout period, complete blood counts and liver function assay tests were performed, and organs were harvested for histology. Potential liver injury caused by the peptide treatment was studied by testing serum AST (Aspartate Aminotransferase) and ALT (Alanine Aminotransferase) levels. No elevation of the two enzymes were observed in the treatment group (FIG. 11B), indicating intact liver function following treatment. Concurrently, no significant change was observed in the blood count (FIG. 11C) in the treatment group. No tissue damage was observed by microscopic examination (FIG. 11D).

Transcriptome Analysis of Differentially Expressed Genes (DEGs)

Figure 12A:
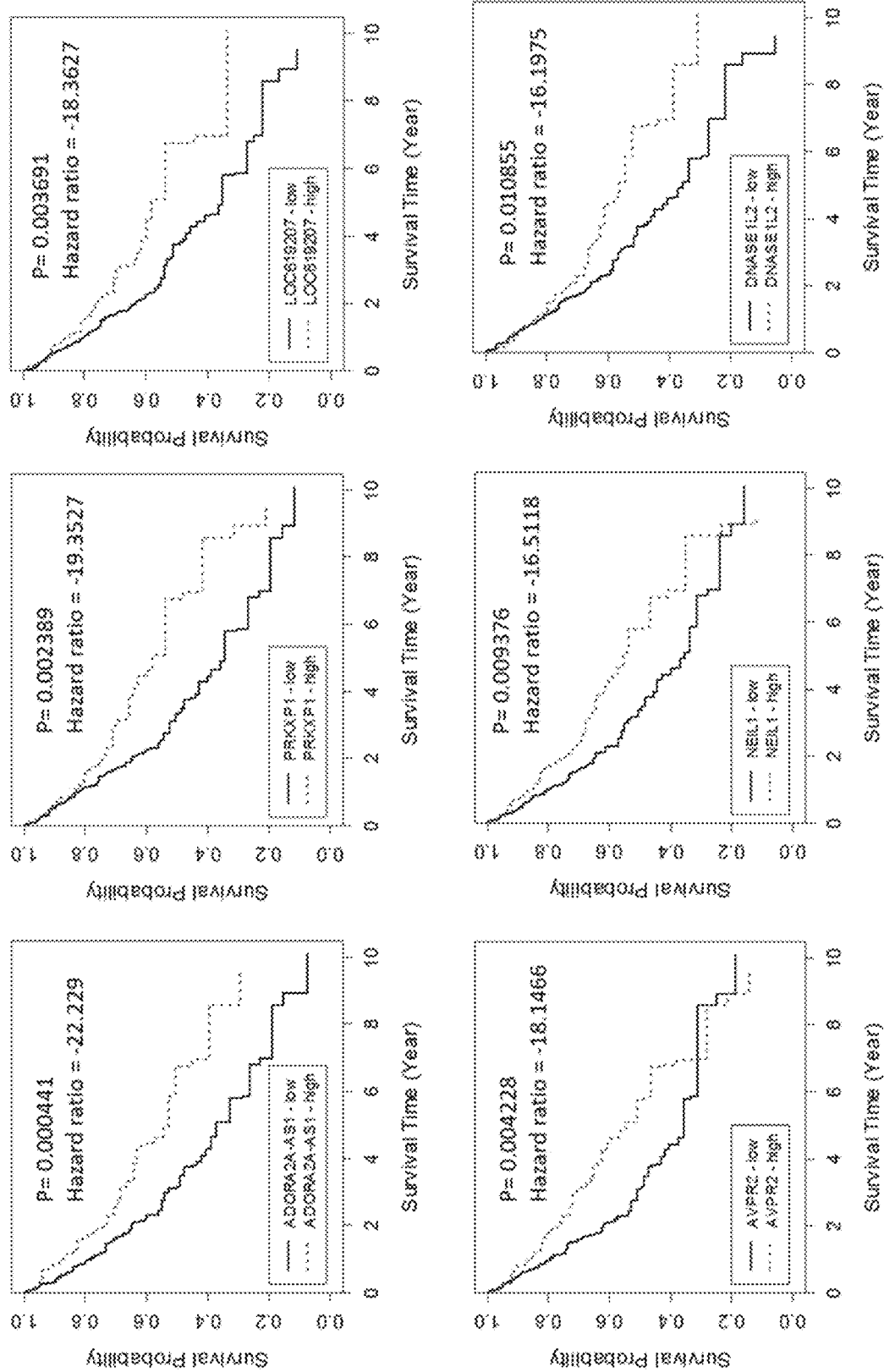
FIGS. 12A-12B Kaplan Meier survival analysis with TCGA HCC patient RNA-seq data set.

Transcriptome analysis showed that more than 99% of the PEN-FFW DEGs were upregulated. These upregulated DEGs were subjected to survival analysis using HCC RNA-seq data from the whole-transcriptome sequencing data of hepatocellular carcinoma, TCGA (n=377) to understand the prognostic value of these upregulated DEGs in patients. Data obtained showed that a subgroup composed of nine genes of the PEN-FFW DEGs predicted patient outcome. Kaplan-Meier analysis of HCC patients with each of the 9-gene subgroup demonstrated that each transcript could predict overall survival of the patients, with significant negative hazard ratio, implying good prognosis were associated with higher expression of the genes (FIG. 12A and Table 3).

TABLE 3

Prognostic value of the individual gene in predicting survival of TCGA HCC patient cohort (n = 377)

| Gene symbol | Description | mean log2 intensity | p value | Hazard ratio | log2 fd FFW/Contr (PEN + Mut) | log2 fd WT/Contr (PEN + Mut) |
| --- | --- | --- | --- | --- | --- | --- |
| ADORA2A-AS1 | adenosine A2a receptor antisense 1 | 10.87653 | 0.00044 | −22.229 | 2.17 | 1.05 |
| PRKXP1 | protein kinase, X-linked, pseudogene 1 | 6.34846 | 0.00239 | −19.353 | 2.12 | 0.62 |
| LOC619207 | scavenger receptor protein family member | 5.64037 | 0.00369 | −18.363 | 1.33 | 0.36 |
| AVPR2 | arginine vasopressin receptor 2 | 3.56679 | 0.00423 | −18.147 | 1.53 | 0.11 |
| NEIL1 | nei endonuclease VIII-like 1 (*E. coli*) | 9.55164 | 0.00938 | −16.512 | 1.11 | 0.30 |
| DNASE1L2 | deoxyribonuclease I-like 2 | 4.91615 | 0.01085 | −16.198 | 1.11 | 0.42 |
| CSAD | cysteine sulfinic acid decarboxylase | 10.98144 | 0.02137 | −14.599 | 1.09 | 0.25 |
| SSPO | SCO-spondin homolog (*Bos taurus*) | 6.54403 | 0.03519 | −13.398 | 2.40 | 0.99 |

Figure 12B:
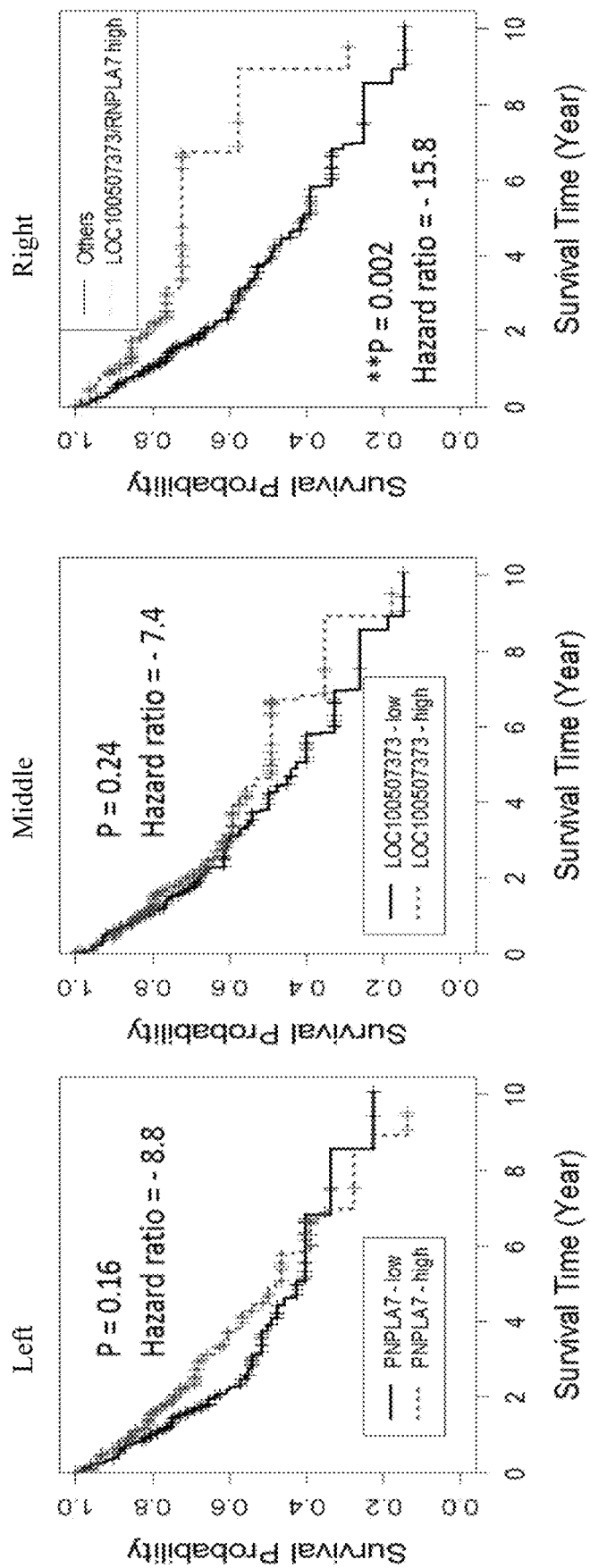

It was observed that PEN-FFW peptide treatment upregulated these DEGs simultaneously. Kaplan-Meier analysis with two-gene combination was performed to analyze the combined risk score of the rest of the PEN-FFW DEGs, as the PEN-FFW peptide treatment upregulated these DEGs simultaneously. 50 combinations of PEN-FFW DEGs that could not predict survival when they used individually (Table 2) was tested. Data obtained demonstrated that these PEN-FFW DEGs that could not predict survival when used individually could now predict overall survival of patients with significant negative hazard ratio (FIG. 12B and Table 4) upon combination with the other upregulated PEN-FFW DEGs. Data obtained suggest that the PEN-FFW DEGs could be used as prognostic markers for predicting a positive and favorable outcome in HCC patients.

TABLE 4

Prognostic value of the individual gene and in combination,
in predicting survival of TCGA HCC patient cohort

| | Gene 1 (alone) | | | Gene 2 (alone) | | Combined | |
|---|---|---|---|---|---|---|---|
| Gene symbol | p value | Hazard ratio | Gene symbol | p value | Hazard ratio | p value | Hazard ratio |
| ZBED3 | 0.1712 | −8.6928 | C5orf4 | 0.0593 | −11.8892 | 0.0005 | −19.9448 |
| NRIP2 | 0.1019 | −10.4024 | ENG | 0.1087 | −10.1582 | 0.0022 | −18.7418 |
| MROH6 | 0.3668 | −5.7450 | ENG | 0.1087 | −10.1582 | 0.0013 | −18.3827 |
| C5orf4 | 0.0593 | −11.8892 | C9orf172 | 0.9196 | −0.6386 | 0.0012 | −17.7766 |
| NOVA2 | 0.1667 | −8.7842 | C5orf4 | 0.0593 | −11.8892 | 0.0020 | −17.6719 |
| DUOX1 | 0.3262 | −6.2508 | C5orf4 | 0.0593 | −11.8892 | 0.0013 | −17.5456 |
| FLJ44511 | 0.4120 | −5.2032 | ENG | 0.1087 | −10.1582 | 0.0027 | −17.4646 |
| PLCH2 | 0.3145 | −6.4062 | NRIP2 | 0.1019 | −10.4024 | 0.0037 | −17.3304 |
| WNK4 | 0.6395 | −2.9707 | C5orf4 | 0.0593 | −11.8892 | 0.0019 | −17.1076 |
| C5orf4 | 0.0593 | −11.8892 | FLJ45340 | 0.4906 | −4.3545 | 0.0023 | −17.0138 |
| TSC2 | 0.3794 | −5.5755 | C5orf4 | 0.0593 | −11.8892 | 0.0032 | −16.8385 |
| SLC26A1 | 0.1442 | −9.3114 | C5orf4 | 0.0593 | −11.8892 | 0.0056 | −16.7979 |
| RGL4 | 0.0998 | −10.4072 | C5orf4 | 0.0593 | −11.8892 | 0.0020 | −16.6570 |
| MLL2 | 0.8555 | 1.1463 | C5orf4 | 0.0593 | −11.8892 | 0.0033 | −16.6457 |
| LOC100288069 | 0.8538 | −1.1701 | C5orf4 | 0.0593 | −11.8892 | 0.0043 | −16.5853 |
| L3MBTL1 | 0.4897 | −4.3837 | ENG | 0.1087 | −10.1582 | 0.0020 | −16.3295 |
| PLCH2 | 0.3145 | −6.4062 | LOC283174 | 0.4031 | −5.3069 | 0.0076 | −16.2819 |
| NOSTRIN | 0.0712 | −11.3461 | LRP5L | 0.0677 | −11.6072 | 0.0046 | −16.2152 |
| NOSTRIN | 0.0712 | −11.3461 | ASIC3 | 0.2220 | −7.7817 | 0.0039 | −16.2092 |
| NOSTRIN | 0.0712 | −11.3461 | LINC00174 | 0.1883 | −8.3553 | 0.0045 | −16.0836 |
| LOC100288123 | 0.1042 | −10.3486 | C5orf4 | 0.0593 | −11.8892 | 0.0050 | −16.0635 |
| LINC00176 | 0.4158 | −5.1747 | ENG | 0.1087 | −10.1582 | 0.0046 | −15.9727 |
| RGL4 | 0.0998 | −10.4072 | CYP2D6 | 0.4189 | −5.1261 | 0.0044 | −15.8806 |
| FN3K | 0.0759 | −11.3178 | NOSTRIN | 0.0712 | −11.3461 | 0.0048 | −15.7906 |
| LOC100507373 | 0.2441 | −7.3646 | PNPLA7 | 0.1642 | −8.8077 | 0.0022 | −15.7870 |
| SYT2 | 0.6049 | −3.2942 | TTYH1 | 0.2414 | −7.4088 | 0.0070 | −15.7508 |
| SRCAP | 0.8212 | 1.4367 | C5orf4 | 0.0593 | −11.8892 | 0.0047 | −15.6613 |
| SRRM2 | 0.4508 | −4.7770 | C5orf4 | 0.0593 | −11.8892 | 0.0057 | −15.6444 |
| LOC284837 | 0.5129 | −4.1606 | SRPK3 | 0.1339 | −9.5455 | 0.0087 | −15.5141 |
| GPR75 | 0.3324 | −6.1444 | SLC26A1 | 0.1442 | −9.3114 | 0.0095 | −15.3751 |
| LRP5L | 0.0677 | −11.6072 | GPR146 | 0.5700 | −3.5962 | 0.0062 | −15.3715 |
| C5orf4 | 0.0593 | −11.8892 | PRRT1 | 0.0932 | −10.6756 | 0.0078 | −15.3447 |
| NRIP2 | 0.1019 | −10.4024 | NOSTRIN | 0.0712 | −11.3461 | 0.0078 | −15.3416 |
| SLC16A8 | 0.3344 | −6.1178 | C5orf4 | 0.0593 | −11.8892 | 0.0080 | −15.2756 |
| NOSTRIN | 0.0712 | −11.3461 | RGL4 | 0.0998 | −10.4072 | 0.0069 | −15.1816 |
| RGL4 | 0.0998 | −10.4072 | ENG | 0.1087 | −10.1582 | 0.0073 | −15.1603 |
| NRIP2 | 0.1019 | −10.4024 | C5orf4 | 0.0593 | −11.8892 | 0.0076 | −15.1595 |
| LRP5L | 0.0677 | −11.6072 | C5orf4 | 0.0593 | −11.8892 | 0.0073 | −15.0790 |
| TTYH1 | 0.2414 | −7.4088 | IDUA | 0.1095 | −10.1935 | 0.0092 | −15.0655 |
| C5orf4 | 0.0593 | −11.8892 | PGAM2 | 0.5130 | −4.1650 | 0.0064 | −15.0482 |
| ZNF154 | 0.9877 | 0.0980 | C5orf4 | 0.0593 | −11.8892 | 0.0095 | −15.0301 |
| GRIN2C | 0.6165 | −3.1861 | TTYH1 | 0.2414 | −7.4088 | 0.0073 | −14.9715 |
| LOC100507373 | 0.2441 | −7.3646 | C5orf4 | 0.0593 | −11.8892 | 0.0050 | −14.9003 |
| TSSK3 | 0.3203 | −6.3125 | PNPLA7 | 0.1642 | −8.8077 | 0.0093 | −14.8663 |
| C9orf96 | 0.8262 | −1.3979 | PNPLA7 | 0.1642 | −8.8077 | 0.0077 | −14.7687 |
| LRP5L | 0.0677 | −11.6072 | PNPLA7 | 0.1642 | −8.8077 | 0.0100 | −14.6966 |
| PRR12 | 0.7417 | 2.0871 | C5orf4 | 0.0593 | −11.8892 | 0.0068 | −14.6264 |
| FN3K | 0.0759 | −11.3178 | FKBP1AP1 | 0.7172 | −2.2997 | 0.0097 | −14.5285 |

Materials and Methods

Isothermal Calorimetry Assay (ITC)

ITC was carried out with an Auto-iTC200 instrument from Microcal Inc. at 25° C. 20 mM of RBBp4 in 50 mM Tris and 100 mM NaCl at pH 7.4 was loaded into the ITC cell. Sal14 peptide at 200 mM was auto-loaded into the syringe. The titration was carried out with 18 injections of 2.4 µl, performed over a period of 30 min with stirring at 1000 rpm. The ITC data was analysed using Origin software from Microcal.

Surface Plasmon Resonance (SPR)

SPR studies were performed using a Biacore T200 biosensor (GE Healthsciences). ~12,000 resonance units (RU) of RBBp4 were immobilised by amine coupling to the carboxymethylated dextran matrix of a Series S CM5 chip (Biacore, GE Healthcare). Multi cycle kinetics analysis was performed at 25° C. through seven injections of SALL4 peptide (0.5 µM-8 µM). The association time and flow rate were set at 60 s and 30 µl/min respectively. The sensograms obtained were of good quality and kinetic rate constants were determined by curve fitting. A running buffer of 50 mM HEPES (pH 7.5), 150 mM NaCl, 0.1% P20, 3% DMSO was used, and KD determination performed using the Biacore T200 Evaluation software (Version 2.0, GE Healthsciences).

Fluorescence Polarization (FP)

Peptides were titrated into a master mix of 0.045 µM RBBp4 and 0.1 µM C-terminal FITC-labelled WT peptide (synthesized by Thermo Scientific). Reactions were incubated at room temperature before the plate was read with an Envision instrument (Perkin Elmer). $IC_{50}$ values of peptides were determined using Prism (GraphPad).

Crystallization and Structure Determination

Crystallization screens were performed with the hanging drop vapor diffusion method using Hampton Research screens. The RBBP4 protein was purchased from SinoBiological and concentrated to 8 mg/ml in 50 mM Tris 100 mM NaCl. The concentrated RBBP4 protein was mixed with 20 mM of SALL4 peptide and crystallization drops were set up at a 1:1 ratio. Diffraction quality crystals of RBBP4-SALL4 complexes were obtained from a reservoir solution containing 0.2M Sodium Chloride, 0.1M Bis-Tris, pH 5.5, 25% PEG 3,350 (Index screen 70). Crystals were grown up to 3 weeks at 4° C. and were cryo-protected by supplementation with 25% (w/v) glycerol. The RBBP4-SALL4 complex crystal diffracted up to 2.7 Å resolution and belonged to the P21 space group. A complete data set was collected using an in-house Saturn944 CCD detector mounted on a Rigaku 007 HFX-ray generator. The data set was processed and scaled using HKL2000. The structure of RBBP4-SALL4 complex was determined by the molecular replacement method using Phenix_Phaser (24). The coordinates of the RbAp48 structure (PDB code 2XU7) was used as a search model. There were two RBBP4-SALL4 complex molecules present in the asymmetric unit. The resultant electron density map was of good quality. Several cycles of model building/refitting using the program Coot (25), and alternated with refinement using the program Phenix-Refine (26) resulted the final model with an R-value of 0.20 (Rfree=0.25) up to 2.7 Å resolution and has good stereo-chemical parameters.

Computational Alanine Scanning

Computational alanine scanning (CAS) was carried out on all 12 residues of the SALL4 peptide. The difference in the binding free energy ($\Delta\Delta G_{bind}$) of the alanine mutants ($\Delta$Gmutant, Ala7 was mutated to glycine) and wild type ($\Delta$Gwild type) was calculated using the molecular mechanics/generalized Born surface area (MM/GBSA) and averaged over 200 equally-spaced trajectory structures extracted from the last 20 ns of the MD simulation of the RBBP4-SALL4 complex. Binding free energy was calculated based on $\Delta\Delta G_{bind}=\Delta$Gmutant-$\Delta$Gwild type.

All programs used for MM/GBSA calculations were part of the AMBER 11 software suite. Molecular mechanical energies were calculated with the sander module. The polar contribution to the solvation free energy was calculated by the pbsa program using the modified GB model described by Onufriev et al. (27) while the nonpolar contribution was estimated from the solvent accessible surface area using the linear combinations of pairwise overlaps method with y set to 0.0072 kcal mol-1 Å-2 and 3 to zero. The entropy term was neglected due to the high computational cost and the assumption that the entropy of the mutant does not differ considerably from that of the wild type. In this analysis, the contribution of each peptide residue to the binding was evaluated by mutating it to alanine in silico and then calculating the difference in free energy of binding ($\Delta\Delta G$) between the mutant and wild-type complexes. The energies were averaged over snapshots extracted from a 50-ns molecular dynamics trajectory of the RBBP4-SALL4 complex.

Cell Culture and Treatment with Peptide

SNU398 was grown in RPMI supplemented with 10% fetal bovine serum (FBS) at 37° C. in a humidified atmosphere of 5% CO2. 3000 cells were seeded in each well of a 96 well plate with 100 µL of medium. Before peptide treatment, cells were washed twice with PBS and treated with different concentrations of peptide in OPTIMEM (LifeTech). Media was added after 4 hrs of incubation at 37° C., and cells incubated for another 68 hrs. Tetrazolium (CellTiter96 AQueous One Solution Cell Proliferation Assay, Promega) was added after 72 hrs incubation with the peptides, and the plate was read at a plate reader at 490 nm after 1 hr of incubation in the dark at 37° C.

Xenograft Studies

All mice were treated in accordance with Responsible Care and Use of Laboratory animals. In the SNU398 in vivo studies, 6-8-week-old female C.B-17 severe combined immunodeficient (SCID) mice (NSG) were inoculated s.c. into the flank with 7.2×105 cells in 2:1 PBS/Matrigel (BD Biosciences). The tumours were then allowed to develop to the size of 50-70 mm3 before intraperitoneal injections of the different peptides were given at two to three-day intervals for a total of 5 injections. Mice were randomly grouped in sets of six and treated with PEN (penetratin control), PEN-MUT (mutant control), PEN-WT (wild type control) and PEN-FFW (peptide 47). Tumor volumes were measured every 5 days and tumor weight were measured at the end point. For PEN control, 22.5 mg/kg were given; for PEN-MUT, PEN-WT and PEN-FFW, 35.6 mg/kg, 37 mg/kg and 36 mg/kg were given respectively to the mice according to their body weight Tumor measurements were taken twice weekly using Vernier calipers. Tumor volume was estimated using the following formula: V=0.5×width×width×length. When tumors approached ~50 mm3, mice were randomized into groups of 5 animals each and received peptides treatment three times weekly by i.p. injection. All statistical analysis was done using a one-way ANOVA and Student's T-test.

Toxicology Study 6-8-week old female C57BL mice were given PEN-FFW (30 mg/kg) (n=3) or DMSO control (n=2) every alternate day, for a total of 17 day, to a cumulative dose of 270 mg/kg. The mice were observed and weighted throughout the period. A 7 days wash out period were given before the mice were sacrificed with their blood and organs collected. Blood count were perform immediately with Celltact MEK6450 (Nihon Kohden, Japan), and serum were subjected for ALT and AST assay on the same day. ALT and AST were performed according to the manufacturer's protocol (Sigma-Aldrich, Merck, Germany). The organs were fixed with neutral buffered Formalin and embedded in paraffin. The tissue sections were then examined by qualified pathologist.

Plasma Stability of PEN-FFW

Plasma stability assay was performed by Cyprotex (Chesire, UK). PEN-FFW was incubated with human plasma (pH7.4) at 37° C. over a 24 hour period (5 timepoints). Incubations were performed at a concentration of 1 µM (final DMSO concentration 2.5%). Reactions were terminated at 0, 5, 10, 15, 30 min, or 0, 1, 2, 4 and 24 hour, by addition of 2 volumes of methanol containing 1% Formic acid. The samples were centrifuged (2500 rpm, 45 min, 4° C.) and the supernatants diluted with 2 volumes of 0.2% Formic acid (aq) (containing Metoprolol (internal standard)). These were then analyzed for PEN-FFW by LC-MS/MS. The percentage of parent peptide remaining at each time point relative to the 0 min sample was calculated from LC-MS/MS peak area ratios (compound peak area/internal standard peak area).

Live Cell Imaging

SNU398 were incubated with Hoechst 33342 for 5 min, washed and incubated with media containing 7.5 uM FITC-PEN-FFW. Time lapse photographs were obtained using Zeiss AxioObserver Live Cell Imager at 2 min interval for the first 1 hr, and 5 min interval for the subsequent 23 hr, with a 20× objective. Image were analyzed with ZEN microscope and imaging software from Zeiss.

RNA-Seq Data Analysis

SNU398 were treated PEN, PEN-MUT, PEN-WT & PEN-FFW for 8 hrs and paired-end RNA-seq was performed for the treated samples. RNA-seq reads of each sample were mapped to hg19 using the STAR aligner. Normalization between the samples was based on the proportionality of the numbers of the mapped reads. The expression fold change of a transcript was obtained using linear regression of the reads between the two samples cross all exons. Differential expression between two samples was selected by using the fold change cut off of 2. Hierarchical clustering was performed based on average linkage to generate the clustering tree as well as heat maps. For identification of enriched gene sets or pathways, Gene Set Enrichment Analysis (GSEA) was performed based on the normalized data and using the GSEA tool (broad.mit.edu/gsea/) with msigdb.v5.0.

Quantitative Realtime PCR

Tumors resected from mice were homogenized in Trizol. Total RNA was extracted and treated with RNase-free DNase (Qiagen). Reverse transcription was carried out using Superscript III Reverse Transcriptase. Quantitative PCR was performed using GoTaq qPCR Master Mix (Promega). Amplification was done with a Corbett Rotor Gene 6000 (Qiagen). Each sample was assayed in triplicate. Primer sequences used are indicated below:

```
                                       (SEQ ID NO: 47)
PTEN forward (F): ACTATTCCCAGTCAGAGGCG (SEQ ID NO: 48)
PTEN reverse (R): GAACTTGTCTTCCCGTCGTG (SEQ ID NO: 49)
18s F: TTAAGAGGGACGGCCGGGGG (SEQ ID NO: 50)
18s R: CATCGCCGGTCGGCATCGTT (SEQ ID NO: 51)
LRRC4 F: CCAGTGCTTTCCTGCCTTC (SEQ ID NO: 52)
LRRC4 R: GCTGCACACAGAATCCACAC (SEQ ID NO: 53)
FAM229A F: AGGAACGTGCTCTGTGAGGT (SEQ ID NO: 54)
FAM229A R: GGCCTCAATGGGGAATCT (SEQ ID NO: 55)
PLIN4 F: CCGGATGTGCTCAGTGTAGG (SEQ ID NO: 56)
PLIN4 R: TTCATGGGGTGGAAGATGTC (SEQ ID NO: 57)
MLL2 F: GTGCAGCAGAAGATGGTGAA (SEQ ID NO: 58)
MLL2 R: GCACAATGCTGTCAGGAGAA (SEQ ID NO: 59)
ANKRD30BL F: AACACCTGACACGGCTGAAA (SEQ ID NO: 60)
ANKRD30BL R: TCCCCCTCTTGAATTTTAAAGGAT (SEQ ID NO: 1)
LOC284801 F: GGAGGTGCTTTGCCTCTGAA (SEQ ID NO: 61)
LOC284801 R: GGTACCAGCACAGTTGGACT
```

We claim:

1. A peptide having less than 12 residues, comprising: the amino acid sequence set forth in formula I $$RRKX_1X_2X_3X_4X_5X_6X_7 \text{(SEQ ID NO: 62)}, \quad (I)$$

wherein $X_1$, $X_2$, $X_3$, $X_4$, $X_5$, $X_6$ or $X_7$ is independently an amino acid with non-polar side chain, polar side chain that is not charged at neutral pH or polar side chain that is positively charged at neutral pH; wherein the peptide does not consist of the amino acid sequence of RRKQAKPQHI (SEQ ID NO: 3); wherein the sequence of amino acids is written from the N-terminus to the C-terminus; and wherein the peptide has an N-terminal acetyl group or protecting group, a C-terminal amine group or protecting group, or both.

2. The peptide of claim 1, wherein the peptide comprises the amino acid sequence set forth in formula II $$A-X_0RRKX_1X_2X_3X_4X_5X_6X_7-B \text{ (SEQ ID NO: 63)}, \quad (II)$$

wherein $X_0$, $X_1$, $X_2$, $X_3$, $X_4$, $X_5$, $X_6$ or $X_7$ is independently an amino acid with non-polar side chain, polar side chain that is not charged at neutral pH or polar side chain that is positively charged at neutral pH;

wherein A is an acetyl group or an N-terminal protecting group;

wherein B is an amine group or a C-terminal protecting group.

3. The peptide of claim 2, wherein $X_0$ is an amino acid with a non-polar side chain or a polar side chain that is positively charged at neutral pH.

4. The peptide of claim 1, wherein the peptide binds to the histone binding protein retinoblastoma binding protein 4 (RBBp4).

5. The peptide of claim 4, wherein the peptide binds to RBBp4 with dissociation constant of about 1 μM or lower.

6. The peptide of claim 5, wherein the peptide is

RRKAAKPQHI, RRKFAKPQHI, RRKFAKFQWI,

RRKQKKPQHI, RRKQRKPQHI, RRKQAAPQHI, RRKQAVPQHI,

RRKQALPQHI, RRKQAFPQHI, RRKQARPQHI, RRKQAKFQHI,

RRKQAKPAHI, RRKQAKPEHI, RRKQAKPNHI, RRKQAKPVHI,

RRKQAKPLHI, RRKQAKPQAI, RRKQAKPQFI, RRKQAKPQYI,

RRKQAKPQWI, RRKQAKPQVI, RRKQAKPQHA, RRKQAKPQHV,

RRKQAKPQHL, RRKQAKPQHF, RRKFAKFQWI, RRKHAKPQHI,

ORRKQAKPQHI, HRRKQAKPQHI, RRKQPKPQHI, HRRKQAKPQHI,

URRKQAKPQHI or

ZRRKQAKPQHI, ORRKHPKPQH.

7. The peptide of claim 4, wherein the molecular weight of the peptide is between about 0.9 to 1.5 kDa.

8. The peptide of claim 1, wherein the peptide comprises the amino acid sequence set forth in RRKX$_1$AKPQHI (SEQ ID NO: 4), wherein $X_1$ is an amino acid with a non-polar aromatic side chain.

9. The peptide of claim 1, wherein the peptide comprises the amino acid sequence set forth in RRKQX$_2$KPQHI (SEQ ID NO: 5), wherein $X_2$ is an amino acid with a polar side chain that is positively charged at neutral pH.

10. The peptide of claim 1, wherein the peptide comprises the amino acid sequence set forth in RRKQAX$_3$PQHI (SEQ ID NO: 6), wherein $X_3$ is an amino acid with a non-polar side chain, or a polar side chain that is positively charged at neutral pH.

11. The peptide of claim 1, wherein the peptide comprises the amino acid sequence set forth in RRKQAKX$_4$QHI (SEQ ID NO: 7), wherein $X_4$ is an amino acid with a non-polar side chain.

12. The peptide of claim 1, wherein the peptide comprises the amino acid sequence set forth in RRKQAKPX$_5$HI (SEQ ID NO: 8) wherein X$_5$ is an amino acid with a non-polar side chain, or a polar side chain that is not charged at neutral pH.

13. The peptide of claim 1, wherein the peptide comprises the amino acid sequence set forth in RRKQAKPQX$_6$I (SEQ ID NO: 9) wherein X$_6$ is an amino acid with a non-polar side chain.

14. The peptide of claim 1, wherein the peptide comprises the amino acid sequence set forth in RRKQAKPQHX$_7$ (SEQ ID NO: 10), wherein X$_7$ is an amino acid with a non-polar side chain.

15. The peptide of claim 1, wherein the peptide comprises the amino acid sequence set forth in RRKX$_1$AKX$_4$QX$_6$I (SEQ ID NO: 11), wherein X$_1$, X$_4$ or X$_6$ is independently selected from a group consisting of amino acids with non-polar side chains.

16. The peptide of claim 15, wherein the peptide comprises the amino acid sequence set forth in X$_0$RRKQAKPQHI (SEQ ID NO: 12), wherein X$_0$ is an amino acid with a non-polar side chain or a polar side chain that is positively charged at neutral pH.

17. A peptide, comprising the peptide of claim 1 and a cell-penetrating peptide attached thereto.

18. The peptide of claim 17, having a molecular weight between about 2.2 to about 3.8 kDa.

19. The peptide of claim 17, wherein the cell-penetrating peptide is attached to the N-terminus of the peptide.

20. The peptide of claim 19, wherein the cell-penetrating peptide comprises an amino acid sequence set forth in RQIKIWFQNRRMKWKK (SEQ ID NO: 2).

21. A peptide comprising a binding peptide and a cell-penetrating peptide attached thereto, wherein the binding peptide:
a) has less than 12 residues;
b) does not consist of RRKQAKPQHI (SEQ ID NO: 3); and
c) comprises the amino acid sequence set forth in formula I

RRKX$_1$X$_2$X$_3$X$_4$X$_5$X$_6$X$_7$(SEQ ID NO: 62), (I)

wherein:
i) X$_1$, X$_2$, X$_3$, X$_4$, X$_5$, X$_6$ or X$_7$ is independently an amino acid with non-polar side chain, polar side chain that is not charged at neutral pH or polar side chain that is positively charged at neutral pH; and ii) the sequence of amino acids is written from the N-terminus to the C-terminus.

22. A pharmaceutical composition comprising the peptide of claim 21 and a pharmaceutically acceptable carrier.

23. The pharmaceutical composition of claim 22, wherein the cell-penetrating, peptide comprises an amino acid sequence RQIKIWIFQNRRNIKWKK (SEQ ID NO: 2).

24. The peptide of claim 21, having a molecular weight of between about 2.2 to about 3.8 kDa.

25. The peptide of claim 21, wherein the cell-penetrating peptide is attached to the N-terminus of the binding peptide.

26. The peptide of claim 25, wherein the cell-penetrating peptide comprises an amino acid sequence set forth in RQIKIWFQNRRMKWKK (SEQ ID NO: 2).

27. A method of inhibiting the binding of a Sal-like protein 4 (SALL4) with histone-binding protein retinoblastoma binding protein 4 (RBBp4) in a cell expressing SALL4, comprising contacting the cells with a peptide comprising a binding peptide having less than 12 residues, wherein the binding peptide comprises the amino acid sequence set forth in formula I

RRKX$_1$X$_2$X$_3$X$_4$X$_5$X$_6$X$_7$(SEQ ID NO: 62) (I), wherein X$_1$, X$_2$, X$_3$, X$_4$, X$_5$, X$_6$ or X$_7$ is independently an amino acid with non-polar side chain, polar side chain that is not charged at neutral pH or polar side chain that is positively charged at neutral pH; wherein the peptide does not consist of the amino acid sequence of RRKQAKPQHI (SEQ ID NO: 3); and wherein the sequence of amino acids is written from the N-terminus to the C-terminus.

28. The method of claim 27, wherein the peptide further comprises a cell-penetrating peptide attached to the binding peptide.

29. The method of claim 27, wherein the binding peptide has an N-terminal acetyl group or protecting group, a C-terminal amine group or protecting group, or both.

30. The method of claim 29, wherein the peptide further comprises a cell-penetrating peptide attached to the binding peptide.

31. A method for treating a subject having a liver cancer mediated by a dysregulation of Sal-like protein 4 (SALL4), comprising administering a therapeutically effective amount of the pharmaceutical composition of claim 22 to the subject in need thereof, thereby treating the subject having the liver cancer mediated by SALL4 dysregulation.

* * * * *

UNITED STATES PATENT AND TRADEMARK OFFICE
CERTIFICATE OF CORRECTION

PATENT NO. : 10,793,601 B2
APPLICATION NO. : 16/095603
DATED : October 6, 2020
INVENTOR(S) : Bee Hui Liu et al.

It is certified that error appears in the above-identified patent and that said Letters Patent is hereby corrected as shown below:

On the Title Page

Item (56), Column 2 (Other Publications), Line 1, delete ""THe Exchageability" and insert -- "The Exchangeability --

In the Claims

In Column 61, Line 33 (approx.), Claim 1, delete "RRKX$_1$X$_2$X$_3$X$_4$X$_5$X$_6$X$_7$(SEQ ID NO: 62)," and insert -- RRKX$_1$X$_2$X$_3$X$_4$X$_5$X$_6$X$_7$ (SEQ ID NO: 62), --

In Column 62, Lines 32-48 (approx.), Claim 6, delete "RRKAAKPQHI, RRKFAKPQHI, RRKFAKFQWI, RRKQKKPQHI, RRKQRKPQHI, RRKQAAPQHI, RRKQAVPQHI, RRKQALPQHI, RRKQAFPQHI, RRKQARPQHI, RRKQAKFQHI, RRKQAKPAHI, RRKQAKPEHI, RRKQAKPNHI, RRKQAKPVHI, RRKQAKPLHI, RRKQAKPQAI, RRKQAKPQFI, RRKQAKPQYI, RRKQAKPQWI, RRKQAKPQVI, RRKQAKPQHA, RRKQAKPQHV, RRKQAKPQHL, RRKQAKPQHF, RRKFAKFQWI, RRKHAKPQHI, ORRKQAKPQHI, HRRKQAKPQHI, RRKQPKPQHI, RRKQAKPQHI, URRKQAKPQHI or ZRRKQAKPQHI, ORRKHPKPQH." and insert -- RRKAAKPQHI (SEQ ID NO: 15), RRKFAKPQHI (SEQ ID NO: 16), RRKFAKFQWI (SEQ ID NO: 39), RRKQKKPQHI (SEQ ID NO: 17), RRKQRKPQHI (SEQ ID NO: 18), RRKQAAPQHI (SEQ ID NO: 19), RRKQAVPQHI (SEQ ID NO: 20), RRKQALPQHI (SEQ ID NO: 21), RRKQAFPQHI (SEQ ID NO: 22), RRKQARPQHI (SEQ ID NO: 23), RRKQAKFQHI (SEQ ID NO: 24), RRKQAKPAHI (SEQ ID NO: 25), RRKQAKPNHI (SEQ ID NO: 27), RRKQAKPVHI (SEQ ID NO: 28), RRKQAKPLHI (SEQ ID NO: 29), RRKQAKPQAI (SEQ ID NO: 30), RRKQAKPQFI (SEQ ID NO: 31), RRKQAKPQWI (SEQ ID NO: 33), RRKQAKPQVI (SEQ ID NO: 34), RRKQAKPQHA (SEQ ID NO: 35), RRKQAKPQHV (SEQ ID NO: 36), RRKQAKPQHL (SEQ ID NO: 37), RRKQAKPQHF (SEQ ID NO: 38), ORRKQAKPQHI (SEQ ID NO: 41), HRRKQAKPQHI (SEQ ID NO: 42), HRRKQAKPQHI (SEQ ID NO: 44), URRKQAKPQHI (SEQ ID NO: 45) or ZRRKQAKPQHI (SEQ ID NO: 46). --

Signed and Sealed this
First Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,793,601 B2

In Column 62, Line 41 (approx.), Claim 21, delete "RRKX$_1$X$_2$X$_3$X$_4$X$_5$X$_6$X$_7$(SEQ ID NO: 62)," and insert -- RRKX$_1$X$_2$X$_3$X$_4$X$_5$X$_6$X$_7$ (SEQ ID NO: 62), --

In Column 64, Line 22 (approx.), Claim 27, delete "RRKX$_1$X$_2$X$_3$X$_4$X$_5$X$_6$X$_7$(SEQ ID NO: 62)," and insert -- RRKX$_1$X$_2$X$_3$X$_4$X$_5$X$_6$X$_7$ (SEQ ID NO: 62), --

SEQUENCE LISTING

```
<160> NUMBER OF SEQ ID NOS: 83

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
ggaggtgctt tgcctctgaa                                              20

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide
```

```
<400> SEQUENCE: 3

Arg Arg Lys Gln Ala Lys Pro Gln His Ile
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 4
<223> OTHER INFORMATION: Xaa = amino acid with non-polar aromatic side
      chain

<400> SEQUENCE: 4

Arg Arg Lys Xaa Ala Lys Pro Gln His Ile
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 5
<223> OTHER INFORMATION: Xaa = polar side chain that is positively
      charged at neutral pH

<400> SEQUENCE: 5

Arg Arg Lys Gln Xaa Lys Pro Gln His Ile
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = amino acid with non-polar side chain or
      polar side chain that is positively charged

<400> SEQUENCE: 6

Arg Arg Lys Gln Ala Xaa Pro Gln His Ile
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 7
<223> OTHER INFORMATION: Xaa = amino acid with non-polar side chain

<400> SEQUENCE: 7

Arg Arg Lys Gln Ala Lys Xaa Gln His Ile
1               5                   10

<210> SEQ ID NO 8
```

```
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 8
<223> OTHER INFORMATION: Xaa = amino acid with non-polar side chain,
      polar side chain that is not charged at neutral pH, or
      polar side chain that is negatively charged at
      neutral pH

<400> SEQUENCE: 8

Arg Arg Lys Gln Ala Lys Pro Xaa His Ile
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 9
<223> OTHER INFORMATION: Xaa = amino acid with non-polar side chain

<400> SEQUENCE: 9

Arg Arg Lys Gln Ala Lys Pro Gln Xaa Ile
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 10
<223> OTHER INFORMATION: Xaa = amino acid with non-polar side chain

<400> SEQUENCE: 10

Arg Arg Lys Gln Ala Lys Pro Gln His Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 4
<223> OTHER INFORMATION: Xaa = amino acid with non-polar side chain
<220> FEATURE:
<221> NAME/KEY: VARIANT
<222> LOCATION: 7
<223> OTHER INFORMATION: Xaa = amino acid with non-polar side chain
<220> FEATURE:
<221> NAME/KEY: VARIANT
<222> LOCATION: 9
<223> OTHER INFORMATION: Xaa = amino acid with non-polar side chain

<400> SEQUENCE: 11

Arg Arg Lys Xaa Ala Lys Xaa Gln Xaa Ile
1               5                   10

<210> SEQ ID NO 12
```

```
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Xaa = amino acid with non-polar side chain or
      polar side chain that is positively charged at
      neutral pH

<400> SEQUENCE: 12

Xaa Arg Arg Lys Gln Ala Lys Pro Gln His Ile
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 13

Met Ser Arg Arg Lys Gln Ala Lys Pro Gln His Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Arg Arg Lys Phe Ala Lys Phe Gln Trp Ile
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 15

Arg Arg Lys Ala Ala Lys Pro Gln His Ile
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 16

Arg Arg Lys Phe Ala Lys Pro Gln His Ile
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 17
```

Arg Arg Lys Gln Lys Lys Pro Gln His Ile
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18

Arg Arg Lys Gln Arg Lys Pro Gln His Ile
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 19

Arg Arg Lys Gln Ala Ala Pro Gln His Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 20

Arg Arg Lys Gln Ala Val Pro Gln His Ile
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 21

Arg Arg Lys Gln Ala Leu Pro Gln His Ile
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 22

Arg Arg Lys Gln Ala Phe Pro Gln His Ile
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 23

Arg Arg Lys Gln Ala Arg Pro Gln His Ile

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 24

Arg Arg Lys Gln Ala Lys Phe Gln His Ile
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 25

Arg Arg Lys Gln Ala Lys Pro Ala His Ile
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 26

Arg Arg Lys Gln Ala Lys Pro Glu His Ile
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Arg Arg Lys Gln Ala Lys Pro Asn His Ile
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 28

Arg Arg Lys Gln Ala Lys Pro Val His Ile
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Arg Arg Lys Gln Ala Lys Pro Leu His Ile
1               5                   10

```
<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

Arg Arg Lys Gln Ala Lys Pro Gln Ala Ile
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 31

Arg Arg Lys Gln Ala Lys Pro Gln Phe Ile
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 32

Arg Arg Lys Gln Ala Lys Pro Gln Tyr Ile
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 33

Arg Arg Lys Gln Ala Lys Pro Gln Trp Ile
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 34

Arg Arg Lys Gln Ala Lys Pro Gln Val Ile
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 35

Arg Arg Lys Gln Ala Lys Pro Gln His Ala
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 36

Arg Arg Lys Gln Ala Lys Pro Gln His Val
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 37

Arg Arg Lys Gln Ala Lys Pro Gln His Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 38

Arg Arg Lys Gln Ala Lys Pro Gln His Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 39

Met Ser Ala Arg Ala Gln Ala Lys Pro Gln His Ile
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 40

Arg Arg Lys His Ala Lys Pro Gln His Ile
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Xaa = Ornithine

<400> SEQUENCE: 41
```

Xaa Arg Arg Lys Gln Ala Lys Pro Gln His Ile
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 42

His Arg Arg Lys Gln Ala Lys Pro Gln His Ile
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 43

Arg Arg Lys Gln Pro Lys Pro Gln His Ile
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 44

His Arg Arg Lys Gln Ala Lys Pro Gln His Ile
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Xaa = Selenocysteine

<400> SEQUENCE: 45

Xaa Arg Arg Lys Gln Ala Lys Pro Gln His Ile
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Z = beta lysine

<400> SEQUENCE: 46

Glx Arg Arg Lys Gln Ala Lys Pro Gln His Ile
1               5                   10

<210> SEQ ID NO 47
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 47
actattccca gtcagaggcg                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
gaacttgtct tcccgtcgtg                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
ttaagaggga cggccggggg                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
catcgccggt cggcatcgtt                                              20

<210> SEQ ID NO 51
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 51
ccagtgcttt cctgccttc                                               19

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
gctgcacaca gaatccacac                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
```

```
aggaacgtgc tctgtgaggt                                              20

<210> SEQ ID NO 54
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 54
ggcctcaatg gggaatct                                                18

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
ccggatgtgc tcagtgtagg                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
ttcatggggt ggaagatgtc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
gtgcagcaga agatggtgaa                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
gcacaatgct gtcaggagaa                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
aacacctgac acggctgaaa                                              20

<210> SEQ ID NO 60
<211> LENGTH: 24
<212> TYPE: DNA
<213> ORGANISM: Artificial Sequence
```

```
<220> FEATURE:
<223> OTHER INFORMATION: Synthetic Oligonucleotide

<400> SEQUENCE: 60
tcccctctct tgaattttaaa ggat                                              24

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
ggtaccagca cagttggact                                                    20

<210> SEQ ID NO 62
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (4)...(10)
<223> OTHER INFORMATION: Xaa = amino acid with non-polar side chain,
      polar side chain that is not charged at neutral pH, or
      polar side chain that is positively charged at
      neutral pH

<400> SEQUENCE: 62

Arg Arg Lys Xaa Xaa Xaa Xaa Xaa Xaa Xaa
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)...(1)
<223> OTHER INFORMATION: Xaa = amino acid with non-polar side chain,
      polar side chain that is not charged at neutral pH, or
      polar side chain that is positively charged at
      neutral pH, having an acetyl or a protecting group
<220> FEATURE:
<221> NAME/KEY: VARIANT
<222> LOCATION: (5)...(10)
<223> OTHER INFORMATION: Xaa = amino acid with non-polar side chain,
      polar side chain that is not charged at neutral pH, or
      polar side chain that is positively charged at
      neutral pH
<220> FEATURE:
<221> NAME/KEY: VARIANT
<222> LOCATION: (11)...(11)
<223> OTHER INFORMATION: Xaa = amino acid with non-polar side chain,
      polar side chain that is not charged at neutral pH, or
      polar side chain that is positively charged at
      neutral pH, having an amine or a protecting group

<400> SEQUENCE: 63

Xaa Arg Arg Lys Xaa Xaa Xaa Xaa Xaa Xaa Xaa
1               5                   10

<210> SEQ ID NO 64
<211> LENGTH: 11
<212> TYPE: PRT
<213> ORGANISM: Artificial Sequence
<220> FEATURE:
```

<223> OTHER INFORMATION: Synthetic Peptide

<400> SEQUENCE: 64

Met Ser Arg Arg Lys Gln Ala Lys Pro Gln His
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 65

Met Ser Arg Arg Lys Gln Ala Lys Pro Gln
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 66

Met Ser Arg Arg Lys Gln Ala Lys Pro
1               5

<210> SEQ ID NO 67
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 67

Ser Arg Arg Lys Gln Ala Lys Pro Gln His Ile
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 68

Arg Arg Lys Gln Ala Lys Pro Gln His Ile
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 69

Arg Lys Gln Ala Lys Pro Gln His Ile
1               5

<210> SEQ ID NO 70
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 70

Ala Arg Lys Gln Ala Lys Pro Gln His Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 71

Arg Ala Lys Gln Ala Lys Pro Gln His Ile
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 72

Arg Arg Ala Gln Ala Lys Pro Gln His Ile
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 73

Arg Arg Lys Gln Ala Lys Ala Gln His Ile
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 74

Lys Arg Lys Gln Ala Lys Pro Gln His Ile
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 75

Arg Lys Lys Gln Ala Lys Pro Gln His Ile
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic Peptide

```
<400> SEQUENCE: 76

Arg Arg Arg Gln Ala Lys Pro Gln His Ile
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 77

Arg Arg Lys Glu Ala Lys Pro Gln His Ile
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 78

Arg Arg Lys Asn Ala Lys Pro Gln His Ile
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 79

Arg Arg Lys Val Ala Lys Pro Gln His Ile
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 80

Arg Arg Lys Leu Ala Lys Pro Gln His Ile
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 81

Arg Arg Lys Gln Ala Lys Val Gln His Ile
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 82
```

```
Arg Arg Lys Gln Ala Lys Leu Gln His Ile
1               5                  10

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)...(1)
<223> OTHER INFORMATION: Xaa = amino acid with non-polar side chain,
      polar side chain that is not charged at neutral pH, or
      polar side chain that is positively charged at
      neutral pH
<220> FEATURE:
<221> NAME/KEY: VARIANT
<222> LOCATION: (5)...(11)
<223> OTHER INFORMATION: Xaa = amino acid with non-polar side chain,
      polar side chain that is not charged at neutral pH, or
      polar side chain that is positively charged at
      neutral pH

<400> SEQUENCE: 83

Xaa Arg Arg Lys Xaa Xaa Xaa Xaa Xaa Xaa Xaa
1               5                  10
```